(12) United States Patent
Yen et al.

(10) Patent No.: US 9,265,787 B2
(45) Date of Patent: Feb. 23, 2016

(54) COMBINED INHIBITION OF THE VITAMIN D RECEPTOR AND DNA REPLICATION IN THE TREATMENT OF CANCER

(71) Applicant: Institute for Cancer Research, Philadelphia, PA (US)

(72) Inventors: Timothy J. Yen, Haverford, PA (US); Vikram Bhattacharjee, Philadelphia, PA (US)

(73) Assignee: Institute for Cancer Research, Philadelphia, PA (US)

( * ) Notice: Subject to any disclaimer, the term of this patent is extended or adjusted under 35 U.S.C. 154(b) by 0 days.

(21) Appl. No.: 14/140,597

(22) Filed: Dec. 26, 2013

(65) Prior Publication Data

US 2014/0163087 A1  Jun. 12, 2014

Related U.S. Application Data

(63) Continuation of application No. PCT/US2012/039242, filed on May 24, 2012.

(60) Provisional application No. 61/503,683, filed on Jul. 1, 2011.

(51) Int. Cl.
| | |
|---|---|
| *A61K 31/70* | (2006.01) |
| *C07H 21/02* | (2006.01) |
| *C07H 21/04* | (2006.01) |
| *A61K 31/713* | (2006.01) |
| *A61K 31/7068* | (2006.01) |
| *A61K 31/59* | (2006.01) |
| *C12N 15/113* | (2010.01) |
| *C12Q 1/68* | (2006.01) |
| *A61K 48/00* | (2006.01) |

(52) U.S. Cl.
CPC ............ *A61K 31/713* (2013.01); *A61K 31/59* (2013.01); *A61K 31/7068* (2013.01); *C12N 15/1138* (2013.01); *A61K 48/00* (2013.01); *C12N 2310/14* (2013.01); *C12N 2310/531* (2013.01)

(58) Field of Classification Search
None
See application file for complete search history.

(56) References Cited

U.S. PATENT DOCUMENTS

| | | | |
|---|---|---|---|
| 2002/0183277 A1* | 12/2002 | Binderup ................ 514/50 |
| 2003/0125271 A1 | 7/2003 | Baker et al. | |
| 2004/0152668 A1* | 8/2004 | Barsony .................. 514/64 |
| 2005/0272688 A1 | 12/2005 | Higgins et al. | |
| 2008/0293647 A1 | 11/2008 | Adorini et al. | |
| 2009/0076091 A1 | 3/2009 | Klein et al. | |
| 2009/0149377 A1 | 6/2009 | Takagi et al. | |

OTHER PUBLICATIONS

International Search Report and Written Opinoin issued in PCT/US2012/039242 dated Aug. 1, 2012.
Van Cutsem, E., et al., "Phase III Trial of Gemcitabine Plus Tipifarnib Compared with Gemcitabine Plus Placebo in Advanced Pancreatic Cancer", J. Clin. Oncol., vol. 22, No. 8, Apr. 15, 2004, pp. 1430-1438.
Philip, P., et al., "Consensus Report of the National Cancer Institute Clinical Trials Planning Meeting on Pancreas Cancer Treatment", J. Clin. Oncol., vol. 27, No. 33, Nov. 20, 2009, pp. 5660-5669.
Chiang, K.-C., et al., "Vitamin D for the prevention and treatment of pancreatic cancer", World J. Gastroenterol., Jul. 21, 2009; 15(27): 3349-3354.
Hershberger, P.A., et al., "Calcitriol (1,25-Dihydroxycholecalciferol) Enhances Paclitaxel Antitumor Activity in Vitro and in Vivo and Accelerates Paclitaxel-induced Apoptosis", Clin. Cancer Res., 2001; 7:1043-1051.
Zhang, X., et al., "Growth Suppression of Ovarian Cancer Xenografts in Nude Mice by Vitamin D Analogue EB1089", Clin. Cancer Res., 2005; 11:323-328.
Beer, T.M., et al., "Double-Blinded Ramdomized Study of High-Dose Calcitriol Plus Docetaxel Compared with Placebo Plus Doxetaxel in Androgen-Independent Prostate Cancer: A Report from the ASCENT Investigators", J. Clin. Oncol., vol. 25, No. 6, Feb. 20, 2007, pp. 669-674.
Trump, D.L., et al., "Phase II Trial of High-Dose, Intermittnent Calcitriol (1,25 Dihodroxyvitamin D3) and Dexamethasone in Androgen-Independent Prostate Cancer", Cancer, May 15, 2006, vol. 106, No. 10, pp. 2136-2142.
Moffatt, K.A., et al., "1a,25-Dihydroxyvitamin D3 and Platinum Drugs Act Synergistically to Inhibit the Growth of Prostate Cancer Cell Lines", Clin. Cancer Res., 1999; 5:695-703.
Saito, N., et al., "Highly potent vitamin D receptor antagonists: design, synthesis, and biological evaluation", Chembiochem., Oct. 2006; 7(10):1479-90.
Nigro, JM, et al., "Mutations in the p53 gene occur in diverse human tumour types", Nature, Dec. 7, 1989; 342(6250):705-8.
McElwain, MC, et al., "Vitamin D: an antiproliferative agent with potential for therapy of squamous cell carcinoma", Am. J. Otolaryngol., Sep.-Oct. 1997; 18(5):293-8.
Getzenberg, RH, et al., "Vitamin D inhibition of prostate adenocarcinoma growth and metastasis in the Dunning rat prostate model system", Urology, Dec. 1997; 50(6):999-1006.
Krishnan, AV, et al., "Calcitriol as a chemopreventative and therapeutic agent in prostate cancer: role of anti-inflammatory activity", J. Bone Miner Res., Dec. 2007; 22 Suppl 2:V74-80.
Ordonez-Moran, P., et al., "Vitamin D and cancer: an update of in vitro and in vivo data", Front Biosci., Sep. 1, 2005; 10:2723-49.

(Continued)

*Primary Examiner* — Sean McGarry
(74) *Attorney, Agent, or Firm* — Stradley Ronon Stevens & Young, LLP

(57) ABSTRACT

Methods for treating tumors comprising cells expressing the vitamin D receptor are provided, and comprise inhibiting the expression or the biologic activity of the vitamin D receptor in the tumor cells, and/or inhibiting the expression or the biologic activity of a constituent of the vitamin D receptor signaling pathway in the tumor cells, and administering to the tumor cells an effective amount of gemcitabine.

20 Claims, 13 Drawing Sheets

(56) References Cited

OTHER PUBLICATIONS van den Bemd, GJ, et al., "Vitamin D and vitamin D analogs in cancer treatment", Curr. Drug Targets, Feb. 2002; 3(1): 85-94.
Adorini, L., et al., "Vitamin D receptor agonists, cancer and the immune system: an intricate relationship", Curr. Top Med Chem., 2006; 6(12):1297-301.
Deeb, KK, et al., "Vitamin D signaling pathways in cancer: potential for anticancer therapeutics", Nat. Rev. Cancer, Sep. 2007; 7(9):684-700.
Moore, MJ, "Brief communication: a new combination in the treatment of advanced pancreatic cancer", Semin. Oncol., Dec. 2005; 32(6 Suppl. 8):5-6.
Ylikomi, et al., "Antiproliferative Action of Vitamin D", Vitamins and Hormones, vol. 64, 2002, pp. 357-406. L.
Deeb, et al., "Vitamin D signalling pathways in cancer: potential for anticancer therapeutics", Nature, vol. 7, Sep. 2007, pp. 684-700.
Bouffard, et al., "Kinetic studies on 2',2'-difluorodeoxycytidine (Gemcitabine) with purified human deoxycytidine kinase and cytidine deaminase", Biochem. Pharmacol., May 5, 1993; 45(9): 1857-61 (Abstract Only).

* cited by examiner

SEQUENCE LISTING

```
<160> NUMBER OF SEQ ID NOS: 16

<210> SEQ ID NO 1
<211> LENGTH: 18
<212> TYPE: RNA
<213> ORGANISM: Homo sapiens

<400> SEQUENCE: 1
caaccaagac uacaagua                                                 18

<210> SEQ ID NO 2
<211> LENGTH: 57
<212> TYPE: RNA
<213> ORGANISM: Homo sapiens

<400> SEQUENCE: 2
ccggccucca guucguguga augaucucga gaucauucac acgaacugga gguuuuu      57

<210> SEQ ID NO 3
<211> LENGTH: 57
<212> TYPE: RNA
<213> ORGANISM: Homo sapiens

<400> SEQUENCE: 3
ccggcgaagu guuuggcaau gagaucucga gaucucauug ccaaacacuu cguuuuu      57

<210> SEQ ID NO 4
<211> LENGTH: 19
<212> TYPE: RNA
```

```
<213> ORGANISM: Homo sapiens

<400> SEQUENCE: 4
gcgcaucauu gccauacug                                                19

<210> SEQ ID NO 5
<211> LENGTH: 19
<212> TYPE: RNA
<213> ORGANISM: Homo sapiens

<400> SEQUENCE: 5
ccaacacacu gcagacgua                                                19

<210> SEQ ID NO 6
<211> LENGTH: 19
<212> TYPE: RNA
<213> ORGANISM: Homo sapiens

<400> SEQUENCE: 6
gcaaugagau cuccugacu                                                19

<210> SEQ ID NO 7
<211> LENGTH: 21
<212> TYPE: RNA
<213> ORGANISM: Homo sapiens

<400> SEQUENCE: 7
cgaaguguuu ggcaaugaga u                                             21

<210> SEQ ID NO 8
<211> LENGTH: 19
<212> TYPE: RNA
<213> ORGANISM: Homo sapiens

<400> SEQUENCE: 8
gcaacaguau uucgguaua                                                19

<210> SEQ ID NO 9
<211> LENGTH: 19
<212> TYPE: RNA
<213> ORGANISM: Homo sapiens

<400> SEQUENCE: 9
ggacuucucu ccaguaaac                                                19

<210> SEQ ID NO 10
<211> LENGTH: 19
<212> TYPE: RNA
<213> ORGANISM: Homo sapiens

<400> SEQUENCE: 10
aaagauagau gguacaaca                                                19

<210> SEQ ID NO 11
<211> LENGTH: 19
<212> TYPE: RNA
<213> ORGANISM: Homo sapiens

<400> SEQUENCE: 11
agauaugaag cgugccgua                                                19

<210> SEQ ID NO 12
<211> LENGTH: 19
```

```
<212> TYPE: RNA
<213> ORGANISM: Homo sapiens

<400> SEQUENCE: 12
gagagcagau gauccuuua                                              19

<210> SEQ ID NO 13
<211> LENGTH: 19
<212> TYPE: RNA
<213> ORGANISM: Homo sapiens

<400> SEQUENCE: 13
ggacaagucu cucagcuau                                              19

<210> SEQ ID NO 14
<211> LENGTH: 19
<212> TYPE: RNA
<213> ORGANISM: Homo sapiens

<400> SEQUENCE: 14
gauaucagcu uagacaauu                                              19

<210> SEQ ID NO 15
<211> LENGTH: 19
<212> TYPE: RNA
<213> ORGANISM: Homo sapiens

<400> SEQUENCE: 15
ggacagaacc cgcagauuu                                              19

<210> SEQ ID NO 16
<211> LENGTH: 21
<212> TYPE: RNA
<213> ORGANISM: Homo sapiens

<400> SEQUENCE: 16
gcuaccuauc acagagcaau u                                           21
```

COMBINED INHIBITION OF THE VITAMIN D RECEPTOR AND DNA REPLICATION IN THE TREATMENT OF CANCER

CROSS REFERENCE TO RELATED APPLICATIONS

This application is a continuation of International Application No. PCT/US12/039242, and claims priority to U.S. Provisional Application No. 61/503,683 filed on Jul. 1, 2011, the contents of each are incorporated by reference herein, in their entirety and for all purposes.

REFERENCE TO A SEQUENCE LISTING

This application includes a Sequence Listing submitted electronically as a text file named VDR Sequence Listing.txt, created on May 20, 2012, with a size of 4096 bytes. The Sequence Listing is incorporated by reference herein.

FIELD OF THE INVENTION

The invention relates generally to the field of cancer treatment. More particularly, the invention relates to combination therapies for treating cancer cells expressing the vitamin D receptor, and especially for enhancing the susceptibility of cancer cells to gemcitabine.

BACKGROUND OF THE INVENTION

Various publications, including patents, published applications, technical articles and scholarly articles are cited throughout the specification. Each of these cited publications is incorporated by reference herein, in its entirety and for all purposes.

Pancreatic cancer is the 4th leading cause of cancer deaths in the US and carries the worst prognosis. Ninety-five percent of all pancreatic tumors are adenocarcinomas. Less than 4% of diagnosed patients have 5 year survival or better, with a median survival of only 3 to 6 months.

Generally speaking, pancreatic cancers are notoriously insensitive to the backbone of cancer chemo- and radiation therapy, all of which target processes essential for genome maintenance. Pancreatic adenocarcinomas are highly resistant to conventional chemotherapies and are a major obstacle to improving treatment outcomes. Gemcitabine is a cytotoxic drug that is the first-line therapy for patients with metastatic pancreas cancer because of a modest improvement in survival over other drugs. Gemcitabine, a nucleoside analog that blocks DNA replication, remains the first line therapy for patients with advanced pancreatic cancer. Even with treatment, however, most patients will not survive more than one year.

While early diagnosis will significantly improve treatment options, efforts to enhance chemosensitivity of tumors are equally important. Novel treatment strategies are especially needed given that Phase III trials of various cytotoxic agents in combination with gemcitabine did not show improvement over gemcitabine alone (Van Cutsem E et al. (2004) J. Clin. Oncol. 22:1430-8; Philip P A (2009) J. Clin. Oncol. 27:5660-9; Moore M J (2005) Semin. Oncol. 32:5-6).

SUMMARY OF THE INVENTION

The invention features various methods for treating tumors that comprise cells expressing the vitamin D receptor (VDR). The methods relate to a combination therapy in which the effects of vitamin D receptor signaling are inhibited, and DNA replication and cell proliferation are also inhibited by gemcitabine. The effect of the combination therapy is that tumor cell death is enhanced relative to the level of tumor cell death induced by either gemcitabine or by vitamin D receptor inhibition alone. These methods may be carried out in vivo, in vitro, or in situ, and if carried out in vivo, may be used in accordance with any subject such as a mammal and preferably a human being.

A method for treating a tumor that comprises cells expressing the vitamin D receptor comprises inhibiting the expression of the vitamin D receptor and/or the expression of a constituent of the vitamin D receptor signal pathway such as RXR, RUNX2, ZBTB16, and p21 in the cells, and contacting the cells with an effective amount of gemcitabine. As a result of the inhibition of vitamin D receptor expression or the inhibition of the constituent expression, and the inhibition of DNA replication by gemcitabine, the level of cell death in the tumor is enhanced, preferably statistically significantly enhanced, relative to the level of cell death in a tumor of the same type in which only the expression of the vitamin D receptor or vitamin D receptor signal pathway constituent was inhibited or that were only treated with gemcitabine. The combined treatment results in a synergistic therapeutic benefit. Thus, the methods are useful for effectuating enhanced killing of tumor cells. Enhanced killing may relate, in part, to a reversion of a drug resistance phenotype in the cells, or to an enhanced susceptibility to gemcitabine.

The tumor may be any tumor in which the vitamin D receptor is expressed or expressed at abnormal levels (e.g., overexpressed or overamplified), or in which vitamin D receptor signaling plays a role in some aspect of tumor pathology, including cell proliferation or resistance to gemcitabine therapy. Non-limiting examples of such tumors include tumors of the pancreas, tumors of the breast, tumors of the ovary, tumors of the lung, tumors of the esophagus, tumors of the prostate gland, and tumors of the lymph nodes. The method may further comprise contacting the cells with an effective amount of an agent that inhibits the expression or the biologic activity of a mutant p53 protein. The mutant p53 may comprise one or more of the following mutations, R175H, R248W, R273H, and Y220C, or any other mutation or combination of mutations that disrupts the transactivation function of p53.

Expression of the vitamin D receptor can be inhibited by transforming a cell with a nucleic acid molecule that specifically hybridizes to the mRNA encoding the vitamin D receptor and interferes with translation. Examples of such nucleic acid molecules include, but are not limited to, siRNA, shRNA, and antisense RNA.

A method for treating a tumor that comprises cells expressing the vitamin D receptor comprises inhibiting the biologic activity of the vitamin D receptor in the cells, or inhibiting the biologic activity of a constituent of the vitamin D receptor signaling pathway, including RXR, RUNX2, p21, and BTB-16, and contacting the cells with an effective amount of gemcitabine. As a result of the inhibition of vitamin D receptor or signal pathway constituent biologic activity, and the inhibition of DNA replication by gemcitabine, the level of cell death in the tumor is enhanced, preferably statistically significantly enhanced, relative to the level of cell death in a tumor of the same type in which only the biologic activity of the vitamin D receptor or signal pathway constituent was inhibited or that were only treated with gemcitabine. The combined treatment results in a synergistic therapeutic benefit. Thus, the methods are useful for effectuating enhanced killing of tumor cells.

Enhanced killing may relate, in part, to a reversion of a drug resistance phenotype in the cells, or to an enhanced susceptibility to gemcitabine.

Inhibition of the biologic activity of the vitamin D receptor can be effectuated by contacting the cell with an agent, which can be a chemical compound, a biomolecule, or a composition thereof, that inhibits the biologic activity of the vitamin D receptor. Any agent known in the art can be used to inhibit the vitamin D receptor, including vitamin D receptor antagonists, which include vitamin D analogs and vitamin D3 analogs. Preferred categories of biomolecules include antibodies and regulatory peptides.

The invention also features methods treating a malignancy of the pancreas, lung, bladder, prostate gland, breast, ovary, lymph nodes, or esophagus that comprises cells which express or overexpress the vitamin D receptor. These methods also relate to a combination therapy in which two aspects of cell metabolism are inhibited—inhibiting the expression or the biologic activity of the vitamin D receptor, and inhibiting DNA replication through gemcitabine. Such methods are carried out in vivo, on any subject in need of such treatment, such as a laboratory animal or a human being.

A method for treating a malignancy of the pancreas, lung, bladder, prostate gland, breast, ovary, lymph nodes, or esophagus comprising cells expressing the vitamin D receptor, comprises transforming a malignant cell of the pancreas, lung, bladder, prostate gland, breast, ovary, lymph nodes, or esophagus expressing the vitamin D receptor in a subject in need thereof with a nucleic acid molecule capable of interfering with the expression of the vitamin D receptor or a nucleic acid molecule capable of interfering with the expression of a constituent of the vitamin D receptor signaling pathway, including RXR, RUNX2, p21, and BTB-16, such that the nucleic acid molecule interferes with the expression of the vitamin D receptor or the constituent upon transformation, and administering to the subject an effective amount of gemcitabine. The method may further comprise administering to the subject an effective amount of an agent that inhibits the expression or the biologic activity of a mutant p53 protein. The mutant p53 may comprise one or more of the following mutations, R175H, R248W, R273H, and Y220C. The subject may be any animal, including mammals. Preferably, the subject is a human being. The nucleic acid molecule may be a siRNA that specifically hybridizes under stringent conditions with vitamin D receptor mRNA or vitamin D receptor signal pathway constituent mRNA.

A method for treating a malignancy of the pancreas, lung, bladder, prostate gland, breast, ovary, lymph nodes, or esophagus comprising cells expressing the vitamin D receptor, comprises administering to a subject in need thereof an effective amount of a nucleic acid molecule capable of interfering with the expression of the vitamin D receptor or a nucleic acid molecule capable of interfering with the expression of a constituent of the vitamin D receptor signaling pathway, including RXR, RUNX2, p21, and ZBTB16, such that the nucleic acid molecule transforms a malignant cell of the pancreas, lung, bladder, prostate gland, breast, ovary, lymph nodes, or esophagus expressing the vitamin D receptor and interferes with the expression of the vitamin D receptor or the constituent upon transformation, and administering to the subject an effective amount of gemcitabine. The method may further comprise administering to the subject an effective amount of an agent that inhibits the expression or the biologic activity of a mutant p53 protein. The mutant p53 may comprise one or more of the following mutations, R175H, R248W, R273H, and Y220C. The subject may be any animal, including mammals. Preferably, the subject is a human being. The nucleic acid molecule may be a siRNA that specifically hybridizes under stringent conditions with vitamin D receptor mRNA or vitamin D receptor signal pathway constituent mRNA.

A method for treating a malignancy of the pancreas, lung, bladder, prostate gland, breast, ovary, or esophagus comprising cells expressing the vitamin D receptor, comprises administering to a subject in need thereof an effective amount of an agent that inhibits the biologic activity of the vitamin D receptor, and an effective amount of gemcitabine. The method may further comprise administering to the subject an effective amount of an agent that inhibits the expression or the biologic activity of a mutant p53 protein. The mutant p53 may comprise one or more of the following mutations, R175H, R248W, R273H, and Y220C. The subject may be any animal, including mammals. Preferably, the subject is a human being.

The agent can be a chemical compound, a biomolecule, or a composition thereof, that inhibits the biologic activity of the vitamin D receptor. Any agent known in the art can be used, including those described or exemplified in this specification. Vitamin D receptor antagonists are a preferred category of agents. Antibodies and regulatory peptides are preferred categories of biomolecules.

BRIEF DESCRIPTION OF THE DRAWINGS

FIG. 5A shows a comparison of cells treated with gemcitabine in the presence and absence of UCN01. FIG. 5B shows cells transfected with control or VDR siRNA and treated with gemcitabine. FIG. 5C shows quantitative data comparing cell killing under various treatment conditions.

DETAILED DESCRIPTION OF THE INVENTION

Figure 1:
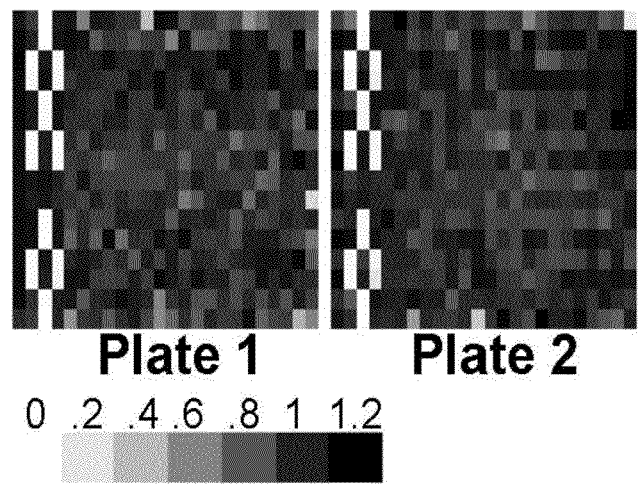
FIG. 1 shows results of a CellTiter-Glo® assay of replicate plates. Scale bar: 0 (white) to 1.2 million (black) light units. Columns 1-4 checkered wells on the left that correspond to the killer and control siRNA controls. Library siRNAs were tested in columns 5-24.

Various terms relating to aspects of the present invention are used throughout the specification and claims. Such terms are to be given their ordinary meaning in the art, unless otherwise indicated. Other specifically defined terms are to be construed in a manner consistent with the definition provided herein.

As used herein, the singular forms "a," "an," and "the" include plural referents unless expressly stated otherwise.

Knockdown includes the reduced expression of a gene. A knockdown typically has at least about a 20% reduction in expression, preferably has at least about a 50% reduction in expression, and more preferably has at least about a 75% reduction in expression, and in some aspects has at least about an 80% to about an 85% reduction in expression, at least about an 85% to about a 90% reduction in expression, or about an 80% to about a 90% reduction in expression, and in some aspects has a greater than 90% reduction in expression, or a greater than 95% reduction in expression.

Transforming includes the introduction of exogenous or heterologous nucleic acid molecules into the cell. Cells may be stably or transiently transformed.

Nucleic acid molecules include any chain of at least two nucleotides, which may be unmodified or modified RNA or DNA, hybrids of RNA and DNA, and may be single, double, or triple stranded.

Expression of a nucleic acid molecule includes the biosynthesis of a gene product, including but not limited to the transcription of a gene into RNA, the translation of RNA into a protein or polypeptide, and all naturally occurring post-transcriptional and post-translational modifications thereof.

Biomolecules include proteins, polypeptides, antibodies, nucleic acid molecules, lipids, monosaccharides, polysaccharides, and all fragments, analogs, homologs, conjugates, and derivatives thereof.

Gemcitabine refers to a compound having Formula I, and all pharmaceutically acceptable salts thereof. Formula I:

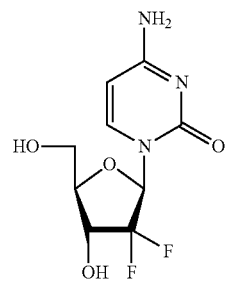

Inhibiting includes interfering with, reducing, decreasing, blocking, preventing, delaying, inactivating, desensitizing, stopping, knocking down (e.g., knockdown), and/or down-regulating the biologic activity or expression of a molecule or pathway of interest.

It has been observed in accordance with the invention that knockdown of expression of the vitamin D receptor (VDR) in cancer cells enhances sensitization of the cells to gemcitabine, with the result of enhanced tumoricidal activity observed in pancreatic tumor cells treated with this combination therapy relative to tumor cells treated with either inhibition or gemcitabine by itself. This observation runs contrary to the conventional understanding in the art that vitamin D has antiproliferative properties such that the vitamin D receptor itself plays a positive role in cancer treatment. Under the conventional understanding, any knockdown or inhibition of the vitamin D receptor would be expected to have a deleterious effect on cancer therapy. Accordingly, the invention features methods for treating tumors comprising cells expressing the vitamin D receptor. The methods may be carried out in vivo, in vitro, or in situ.

In some aspects, a method for treating a tumor comprising cells expressing the vitamin D receptor comprises inhibiting the expression of the vitamin D receptor in the cells and contacting the cells with an effective amount of gemcitabine. In preferred aspects, inhibiting the expression of the vitamin D receptor in the cells enhances the level of gemcitabine-induced cell death in the tumor relative to the level of cell death in a tumor of the same type contacted with gemcitabine in which the expression of the vitamin D receptor was not inhibited. Cell death may be enhanced in tumors resistant to gemcitabine.

In some aspects, a method for treating a tumor comprising cells expressing the vitamin D receptor comprises inhibiting the expression of a constituent of the vitamin D receptor signaling pathway in the cells and contacting the cells with an effective amount of gemcitabine. The constituent may be one or more of retinoid receptor X (RXR), runt related transcription factor 2 (RUNX2), and zinc finger and BTB domain containing 16 (ZBT16). This latter gene is a member of the Krueppel C2H2-type zinc-finger protein family and encodes a zinc finger transcription factor that contains nine Kruppel-type zinc finger domains at the carboxyl terminus. In preferred aspects, inhibiting the expression of the constituent of the vitamin D receptor signaling pathway in the cells enhances the level of gemcitabine-induced cell death in the tumor relative to the level of cell death in a tumor of the same type contacted with gemcitabine in which the expression of the constituent was not inhibited. Cell death may be enhanced in tumors resistant to gemcitabine.

In any of the methods, the expression of the vitamin D receptor or a constituent of the vitamin D receptor signaling pathway can be inhibited, for example, by transforming tumor cells with a nucleic acid molecule that interferes with the expression of the gene encoding the vitamin D receptor or a nucleic acid molecule that interferes with the expression of the gene encoding the constituent of the vitamin D receptor signaling pathway such as RXR, RUNX2, and ZBTB16. Gene expression can be inhibited, for example, through the use of a variety of post-transcriptional gene silencing (RNA silencing) techniques.

RNA interference (RNAi) is a mechanism of post-transcriptional gene silencing mediated by double-stranded RNA (dsRNA), which is distinct from antisense and ribozyme-based approaches. RNA interference may be effectuated, for example, by administering a nucleic acid (e.g., dsRNA) that hybridizes under stringent conditions to the gene encoding the vitamin D receptor, thereby attenuating its expression. RNA interference provides shRNA or siRNA that comprise multiple sequences that target one or more regions of the target gene. dsRNA molecules (shRNA or siRNA) are believed to direct sequence-specific degradation of mRNA in cells of various types after first undergoing processing by an RNase III-like enzyme called DICER into smaller dsRNA molecules comprised of two 21 nucleotide (nt) strands, each of which has a 5' phosphate group and a 3' hydroxyl, and includes a 19 nt region precisely complementary with the other strand, so that there is a 19 nt duplex region flanked by 2 nt-3' overhangs. RNAi is thus mediated by short interfering RNAs (siRNA), which typically comprise a double-stranded region approximately 19 nucleotides in length with 1-2 nucleotide 3' overhangs on each strand, resulting in a total length of between approximately 21 and 23 nucleotides. In mammalian cells, dsRNA longer than approximately 30 nucleotides typically induces nonspecific mRNA degradation via the interferon response. However, the presence of siRNA in mammalian cells, rather than inducing the interferon response, results in sequence-specific gene silencing.

Viral vectors or DNA vectors encode short hairpin RNA (shRNA) which are processed in the cell cytoplasm to short interfering RNA (siRNA). In general, a short, interfering RNA (siRNA) comprises an RNA duplex that is preferably approximately 19 basepairs long and optionally further comprises one or two single-stranded overhangs or loops. A siRNA may comprise two RNA strands hybridized together, or may alternatively comprise a single RNA strand that includes a self-hybridizing portion. siRNAs may include one or more free strand ends, which may include phosphate and/or hydroxyl groups. siRNAs typically include a portion that hybridizes under stringent conditions with a target transcript. One strand of the siRNA (or, the self-hybridizing portion of the siRNA) is typically precisely complementary with a region of the target transcript (e.g., vitamin D receptor transcript), meaning that the siRNA hybridizes to the target transcript without a single mismatch. In aspects in which perfect complementarity is not achieved, it is generally preferred that any mismatches be located at or near the siRNA termini.

siRNAs have been shown to downregulate gene expression when transferred into mammalian cells by such methods as transfection, electroporation, cationic liposome-mediated transfection, or microinjection, or when expressed in cells via any of a variety of plasmid-based approaches. The siRNA may comprise two individual nucleic acid strands or of a single strand with a self-complementary region capable of forming a hairpin (stem-loop) structure. A number of variations in structure, length, number of mismatches, size of loop, identity of nucleotides in overhangs, etc., are consistent with effective siRNA-triggered gene silencing. While not wishing to be bound by any theory, it is believed that intracellular processing (e.g., by DICER) of a variety of different precursors results in production of siRNA capable of effectively mediating gene silencing. Generally, it is preferred to target exons rather than introns, and it may also be preferable to select sequences complementary to regions within the 3' portion of the target transcript. Generally it is preferred to select sequences that contain an approximately equimolar ratio of the different nucleotides and to avoid stretches in which a single residue is repeated multiple times.

siRNAs may thus comprise RNA molecules having a double-stranded region approximately 19 nucleotides in length with 1-2 nucleotide 3' overhangs on each strand, resulting in a total length of between approximately 21 and 23 nucleotides. siRNAs also include various RNA structures that may be processed in vivo to generate such molecules. Such structures include RNA strands containing two complementary elements that hybridize to one another to form a stem, a loop, and optionally an overhang, preferably a 3' overhang. Preferably, the stem is approximately 19 bp long, the loop is about 1-20, more preferably about 4-10, and most preferably about 6-8 nt long and/or the overhang is about 1-20, and more preferably about 2-15 nt long. In certain aspects, the stem is minimally 19 nucleotides in length and may be up to approximately 29 nucleotides in length. Loops of 4 nucleotides or greater are less likely subject to steric constraints than are shorter loops and therefore may be preferred. The overhang may include a 5' phosphate and a 3' hydroxyl. The overhang may, but need not comprise a plurality of U residues, e.g., between 1 and 5 U residues. Classical siRNAs as described above trigger degradation of mRNAs to which they are targeted, thereby also reducing the rate of protein synthesis. In addition to siRNAs that act via the classical pathway, certain siRNAs that bind to the 3' UTR of a template transcript may inhibit expression of a protein encoded by the template transcript by a mechanism related to but distinct from classic RNA interference, e.g., by reducing translation of the transcript rather than decreasing its stability. Such RNAs are referred to as microRNAs (miRNAs) and are typically between approximately 20 and 26 nucleotides in length, e.g., 22 nt in length. It is believed that they are derived from larger precursors known as small temporal RNAs (stRNAs) or mRNA precursors, which are typically approximately 70 nt long with an approximately 4-15 nt loop. Endogenous RNAs of this type have been identified in a number of organisms including mammals, suggesting that this mechanism of post-transcriptional gene silencing may be widespread. MicroRNAs have been shown to block translation of target transcripts containing target sites.

siRNAs such as naturally occurring or artificial (i.e., designed by humans) mRNAs that bind within the 3' UTR (or elsewhere in a target transcript) and inhibit translation may tolerate a larger number of mismatches in the siRNA/template duplex, and particularly may tolerate mismatches within the central region of the duplex. In fact, there is evidence that some mismatches may be desirable or required as naturally occurring stRNAs frequently exhibit such mismatches as do mRNAs that have been shown to inhibit translation in vitro. For example, when hybridized with the target transcript such siRNAs frequently include two stretches of perfect complementarity separated by a region of mismatch. A variety of structures are possible. For example, the mRNA may include multiple areas of nonidentity (mismatch). The areas of nonidentity (mismatch) need not be symmetrical in the sense that both the target (e.g., the vitamin D receptor, vitamin D receptor signal pathway constituent, or mutant p53) and the mRNA include nonpaired nucleotides. Typically the stretches of perfect complementarity are at least 5 nucleotides in length, e.g., 6, 7, or more nucleotides in length, while the regions of mismatch may be, for example, 1, 2, 3, or 4 nucleotides in length.

Hairpin structures designed to mimic siRNAs and mRNA precursors are processed intracellularly into molecules capable of reducing or inhibiting expression of target transcripts (e.g., the vitamin D receptor, vitamin D receptor signal pathway constituent, or mutant p53). These hairpin structures, which are based on classical siRNAs consisting of two RNA strands forming a 19 bp duplex structure are classified as class I or class II hairpins. Class I hairpins incorporate a loop at the 5' or 3' end of the antisense siRNA strand (i.e., the strand complementary to the target transcript whose inhibition is desired) but are otherwise identical to classical siRNAs. Class II hairpins resemble mRNA precursors in that they include a 19 nt duplex region and a loop at either the 3' or 5' end of the antisense strand of the duplex in addition to one or more nucleotide mismatches in the stem. These molecules are processed intracellularly into small RNA duplex structures capable of mediating silencing. They appear to exert their effects through degradation of the target mRNA rather than through translational repression as is thought to be the case for naturally occurring mRNAs and stRNAs.

Thus, a diverse set of RNA molecules containing duplex structures is able to mediate silencing through various mechanisms. Any such RNA, one portion of which binds to a target transcript (e.g., the vitamin D receptor, vitamin D receptor signal pathway constituent, or mutant p53) and reduces its expression, whether by triggering degradation, by inhibiting translation, or by other means, may be considered an siRNA, and any structure that generates such an siRNA (i.e., serves as a precursor to the RNA) is useful.

A further method of RNA interference is the use of short hairpin RNAs (shRNA). A plasmid containing a DNA sequence encoding for a particular desired siRNA sequence is delivered into a target cell via transfection or virally-mediated infection. Once in the cell, the DNA sequence is continuously transcribed into RNA molecules that loop back on themselves and form hairpin structures through intramolecular base pairing. These hairpin structures, once processed by the cell, are equivalent to transfected siRNA molecules and are used by the cell to mediate RNAi of the desired protein. The use of shRNA has an advantage over siRNA transfection as the former can lead to stable, long-term inhibition of protein expression. Inhibition of protein expression by transfected siRNAs is a transient phenomenon that does not occur for times periods longer than several days. In some cases, though, this may be preferable and desired. In cases where longer periods of protein inhibition are necessary, shRNA mediated inhibition is preferable. The use of shRNA is preferred for some aspects of the invention. Typically, siRNA-encoding vectors are constructs comprising a promoter, a sequence of the target gene to be silenced in the sense orientation, a spacer, the antisense of the target gene sequence, and a terminator.

Inhibition of the expression of the vitamin D receptor, a vitamin D receptor signal pathway constituent, or mutant p53 can also be effectuated by other means that are known and readily practiced in the art. For example, antisense nucleic acids can be used. Antisense RNA transcripts have a base sequence complementary to part or all of any other RNA transcript in the same cell. Such transcripts modulate gene expression through a variety of mechanisms including the modulation of RNA splicing, the modulation of RNA transport and the modulation of the translation of mRNA. Accordingly, in certain aspects, inhibition of the expression of the vitamin D receptor in a cell can be accomplished by expressing an antisense nucleic acid molecule in the cell.

Antisense nucleic acids are generally single-stranded nucleic acids (DNA, RNA, modified DNA, or modified RNA) complementary to a portion of a target nucleic acid (e.g., an mRNA transcript) and therefore able to bind to the target to form a duplex. Typically, they are oligonucleotides that range from 15 to 35 nucleotides in length but may range from 10 up to approximately 50 nucleotides in length. Binding typically reduces or inhibits the expression of the target nucleic acid, such as the gene encoding the target signal protein. For example, antisense oligonucleotides may block transcription when bound to genomic DNA, inhibit translation when bound to mRNA, and/or lead to degradation of the nucleic acid. Inhibition of the expression of the vitamin D receptor, a vitamin D receptor signal pathway constituent, or mutant p53 can be achieved by the administration of antisense nucleic acids comprising sequences complementary to those of the mRNA that encodes the vitamin D receptor, the vitamin D receptor signal pathway constituent, or mutant p53.

Antisense oligonucleotides can be synthesized with a base sequence that is complementary to a portion of any RNA transcript in the cell. Antisense oligonucleotides can modulate gene expression through a variety of mechanisms including the modulation of RNA splicing, the modulation of RNA transport and the modulation of the translation of mRNA. Various properties of antisense oligonucleotides including stability, toxicity, tissue distribution, and cellular uptake and binding affinity may be altered through chemical modifications including (i) replacement of the phosphodiester backbone (e.g., peptide nucleic acid, phosphorothioate oligonucleotides, and phosphoramidate oligonucleotides), (ii) modification of the sugar base (e.g., 2'-O-propylribose and 2'-methoxyethoxyribose), and (iii) modification of the nucleoside (e.g., C-5 propynyl U, C-5 thiazole U, and phenoxazine C).

Inhibition of the vitamin D receptor or vitamin D receptor signal pathway constituent can also be effectuated by use of ribozymes. Certain nucleic acid molecules referred to as ribozymes or deoxyribozymes have been shown to catalyze the sequence-specific cleavage of RNA molecules. The cleavage site is determined by complementary pairing of nucleotides in the RNA or DNA enzyme with nucleotides in the target RNA. Thus, RNA and DNA enzymes can be designed to cleave to any RNA molecule, thereby increasing its rate of degradation.

In some aspects, the cells can be specifically transformed with transcription-silencing nucleic acids such as shRNA or siRNA, or can be transformed with vectors encoding such nucleic acids such that the cell expresses the inhibitory nucleic acid molecules. Transformation of the cells can be carried out according to any means suitable in the art.

A cell can be transformed with such nucleic acid molecules according to any means available in the art such as those describe or exemplified herein. It is preferred that cells are stably transformed with a vector comprising a nucleic acid sequence encoding such regulatory nucleic acid molecules, although transiently transformations are suitable. Any vector suitable for transformation of the particular cell of interest can be used. In preferred embodiments, the vector is a viral vector. In some embodiments, the viral vector is a lentivirus vector.

In some aspects, a method for treating a tumor comprising cells expressing the vitamin D receptor comprises inhibiting the biological activity of the vitamin D receptor, a vitamin D receptor signal pathway constituent such as RXR, RUNX2, ZBTB16, and p21, or mutant p53 in the cells and contacting the cells with an effective amount of gemcitabine. In preferred aspects, inhibiting the biological activity of the vitamin D receptor, the vitamin D receptor signal pathway constituent, or mutant p53 in the cells enhances the level of gemcitabine-induced cell death in the tumor relative to the level of cell death in a tumor of the same type contacted with gemcitabine in which the biological activity of the vitamin D receptor, the vitamin D receptor signal pathway constituent, or mutant p53 was not inhibited. Cell death may be enhanced in tumors resistant to gemcitabine.

The biologic activity of the vitamin D receptor, the vitamin D receptor signal pathway constituent, or mutant p53 can be inhibited, for example, by contacting tumor cells with a compound, biomolecule, or composition of a compound or a biomolecule that inhibits the biologic activity of the vitamin D receptor, the vitamin D receptor signal pathway constituent, or mutant p53 in the cell. Preferred biomolecules include peptide inhibitors and antibodies.

Non-limiting examples of compounds that inhibit the biological activity of the vitamin D receptor and/or its signal pathway include vitamin D receptor antagonists, including vitamin D analogs and vitamin D3 analogs that antagonize the vitamin D receptor. Examples of suitable analog antagonists include, but are not limited to TEI-9647, and TEI-9648. Other suitable antagonists include those described in Saito N et al. (2006) Chem. Biochem. 7:1478-90; Deeb K K et al. (2007) Nature 7:684-700; Chiang K-C et al. (2009) World J. Gastroenterol. 15:3349-54.

The methods thus relate to a combination treatment, targeting the vitamin D receptor and targeting DNA and cell replication processes. For the combination, the cells may be contacted with gemcitabine before inhibiting the expression of the vitamin D receptor, substantially contemporaneously with inhibiting the expression of the vitamin D receptor, or preferably, after inhibiting the expression of the vitamin D receptor.

The methods may be used to treat any cancer (or tumor type) in which the vitamin D receptor is expressed, or expressed at abnormal levels, or in which vitamin D receptor signaling mediates cancer development, progression, pathology, or resistance to one or more chemotherapeutic agents. Non-limiting examples of such cancers include pancreatic cancer, lung cancer (including non small cell lung cancer), bladder cancer, breast cancer, ovarian cancer esophageal cancer, prostate cancer, and lymphoma, among others, including any of these cancers in a metastatic stage. Pancreatic cancer is a highly preferred target of the methods.

The invention also features methods for treating a malignancy of the pancreas, lung, bladder, prostate gland, breast, ovary, lymph nodes, or esophagus comprising cells expressing the vitamin D receptor. In some aspects, the methods comprise transforming a malignant cell of the pancreas, lung, bladder, prostate, breast, ovary, lymph nodes, or esophagus in the subject with a nucleic acid molecule that interferes with the expression of the vitamin D receptor, and administering to the subject an effective amount of gemcitabine. Transformation of the cells may be facilitated according to any technique suitable in the art.

In some aspects, the methods comprise administering to a subject in need thereof an effective amount of a nucleic acid molecule that interferes with the expression of the vitamin D receptor and administering to the subject an effective amount of gemcitabine. Following administration of the nucleic acid molecule, the nucleic acid molecule transforms a malignant cell of the pancreas, lung, bladder, breast, ovary, prostate, lymph nodes, or esophagus expressing the vitamin D receptor and interferes with the expression of the gene encoding the vitamin D receptor. The nucleic acid molecule may be administered to or specifically targeted to the cells of interest, or at least to an area proximal to the cells of interest. Transformation of the cells may be facilitated according to any technique suitable in the art.

In some aspects, the methods comprise administering to a subject in need thereof an effective amount of an agent that inhibits the biologic activity of the vitamin D receptor and an effective amount of gemcitabine. The agent that inhibits the biologic activity of the vitamin D receptor may be a compound, biomolecule, or composition comprising a compound or biomolecule that inhibits the biologic activity of the vitamin D receptor in the cell. The compound or biomolecule may be specific to the vitamin D receptor, or may be a non-specific inhibitor. Preferred biomolecules include peptide inhibitors and antibodies. Non-limiting categories of small molecules that inhibit the biologic activity vitamin D receptor include vitamin D analogs.

The agents may be administered according to any technique suitable in the art. The subject to which the agents are administered may be any animal, preferably mammals, and including laboratory animals (e.g., rodents such as mice, rabbits, and rats), companion animals (e.g. cats and dogs), farm animals (e.g., horses, cows, pigs, sheep), and non-human primates. Human beings are preferred subjects.

The methods of treatment include a combination therapy, by targeting both the vitamin D receptor and targeting DNA and cell replication processes. For the combination, the agent for inhibiting the biologic activity of the vitamin D receptor may be administered to the subject before gemcitabine is administered to the subject, may be administered to the subject substantially at the same time as gemcitabine is administered to the subject, or may be administered to the subject after gemcitabine is administered to the subject In any of the methods described above, the methods may further comprise inhibiting the expression or the biologic activity of a mutated p53. Inhibition of the expression of a mutated p53 may be accomplished by the use of regulatory nucleic acids that interfere with the translation of the mutated p53 protein, e.g., as described above. Inhibition of the biologic activity of a mutated p53 may be accomplished by the use of compounds, biomolecules, or compositions comprising compounds or biomolecules that inhibit the biologic activity of the mutated p53. The mutant p53 may comprise one or more of the following mutations, R175H, R248W, R273H, and Y220C, as well as any other mutation known or determined to disrupt a p53 transactivation function. The regulatory nucleic acid may specifically hybridize to a region of the p53 molecule harboring any of these mutations.

The following examples are provided to describe the invention in greater detail. They are intended to illustrate, not to limit, the invention.

Example 1

Identification of the Vitamin D Receptor for Sensitizing Pancreatic Cancer Cells It is believed that the identification of the molecular basis for chemoresistance in pancreatic cancers may provide new approaches to enhance cell killing by cytotoxic agents such as gemcitabine. An unbiased approach was undertaken to conduct a synthetic lethal screen using a genome-wide siRNA library. Synthetic lethality is based on genetic studies in yeast and *Drosophila*, where mutations that disrupt two or more pathways are required to uncover a biological process is specified by multiple overlapping or parallel pathways. It is believed that this concept may be applied to human cancers that harbor specific loss of function mutations in pathways that should render them selectively more sensitive to inhibitors that target pathways on which the cell critically relies. In addition, it is believed that normal cells, which do not harbor the mutation, should not exhibit a synthetic lethal response as compared to the cancer cell.

The screen was to identify siRNA's from a library that would enhance killing of Panc1 cells to a sublethal dose ($IC_{20}$) of gemcitabine. The dose of drug exerted a biological effect as it was sufficient to induce DNA damage and cell cycle arrest. Cells in 384 well plates were transfected with positive, negative and library siRNAs. Forty eight hours later, transfected cells were treated with gemcitabine or vehicle alone for another 24 hours. Cell viability was quantitated with CellTiter-Glo® (Promega Corp., Madison, Wis.), and values were compared between drug and no drug. The assays were performed in duplicate (duplicates for drug and no drug) and experiments with acceptable z-scores (>0.5) were analyzed by an in house Biostatistician. Hits with high statistical confidence and a low false discovery rate (FDR) were selected for validation.

125 candidate genes were selected from the statistical analysis and further evaluated with bioinformatics tools to identify potential pathways and networks. The screen is significant because it is a genome-wide functional-based screen of pancreatic cancer cells. While the caveat of the screen is that it does not take into account the microenvironment of the cancer cell, it is believed that the use of cell lines will identify survival/resistance pathways that are intrinsic to the cell. As detailed below, several components that interact with the vitamin D receptor (VDR) were identified, and the VDR itself was validated as a determinant of gemcitabine sensitivity. The screen therefore identified a pathway for which FDA-approved drugs are available, and uncovered new biology about how pancreatic cancer cells tolerate cytotoxic drugs.

Example 2

Characterization of the Role of the Vitamin D Receptor in Drug Sensitization

The standard of care for pancreatic cancer primarily includes surgery and gemcitabine treatment. Therefore, it is believed that the development of combination therapies should be based on an understanding of the biology of the disease. The screening assay included a genome-wide functional screen to identify genes that enhance survival of pancreatic cancer cells to gemcitabine. This functional screen was a success because it identified components of the DNA damage checkpoint network that is being targeted (e.g., Chk1 inhibitors) to sensitize killing of pancreatic cancer cells by gemcitabine and other cytotoxic agents. This strategy provided a systematic way to identify all of the molecular determinants that allow pancreatic cancer cells to survive gemcitabine treatment. The vitamin D receptor pathway is one such example of a new target identified by the screen for improving the chemosensitivity of pancreatic cancer cells.

Vitamin D is widely known to exhibit anti-proliferative effects in vitro and clinical trials have been conducted as an anti-cancer drug (Adorini L et al. (2006) Curr. Top. Med. Chem. 6:1297-1301; Deeb K K et al. (2007) Nat. Rev. Cancer 7:684-700; and, Chiang K C et al. (2009) World J. Gastroenterol. 15:3349-54). The observations that cell killing by gemcitabine is enhanced after knockdown of the VDR are opposite to the current paradigm where VDR is responsible for the anti-proliferative effects of vitamin D (van den Bemd G J et al. (2002) Curr. Drug Targets 3:85-94; and, Ordonez-Moran P et al. (2005) Front. Biosci 10:2723-49). Vitamin D is thought to exert its anti-proliferative effects through VDR-dependent upregulation of cell cycle inhibitors such as p21, p27, and GADD45, and repression of G1 cyclins. In this model, the VDR plays a positive role in anti-proliferation. By contrast, the present data suggest that the VDR may play a positive role in the survival of pancreatic cancer cells to cytotoxic agents. This represents a shift in the current thinking about the rationale for choosing whether to treat cancer with activators of inhibitors of the VDR pathway.

Example 3

Preliminary Studies

An unbiased genome-wide siRNA screen was conducted on Panc1 cells to identify ways to enhance killing by a sublethal dose of gemcitabine. Panc1 cells were used because they are from a robust cell line for high throughput siRNA transfections. Panc-1 cells are not adenocarcinomas but they share with adenocarcinoma cell lines (CFPAC, BXPC3, MiaPaCa2 and others) very similar molecular responses to gemcitabine and other genotoxic agents. For example, Panc-1 cells, as with adenocarcinomas, respond to gemcitabine by delaying cell cycle progression as a result of stalled replication forks that result in DNA damage. For the screening assay, the dose of drug used was sufficient to induce DNA damage as determined by the presence of phospho-H2AX foci and cell cycle arrest.

Figure 2:
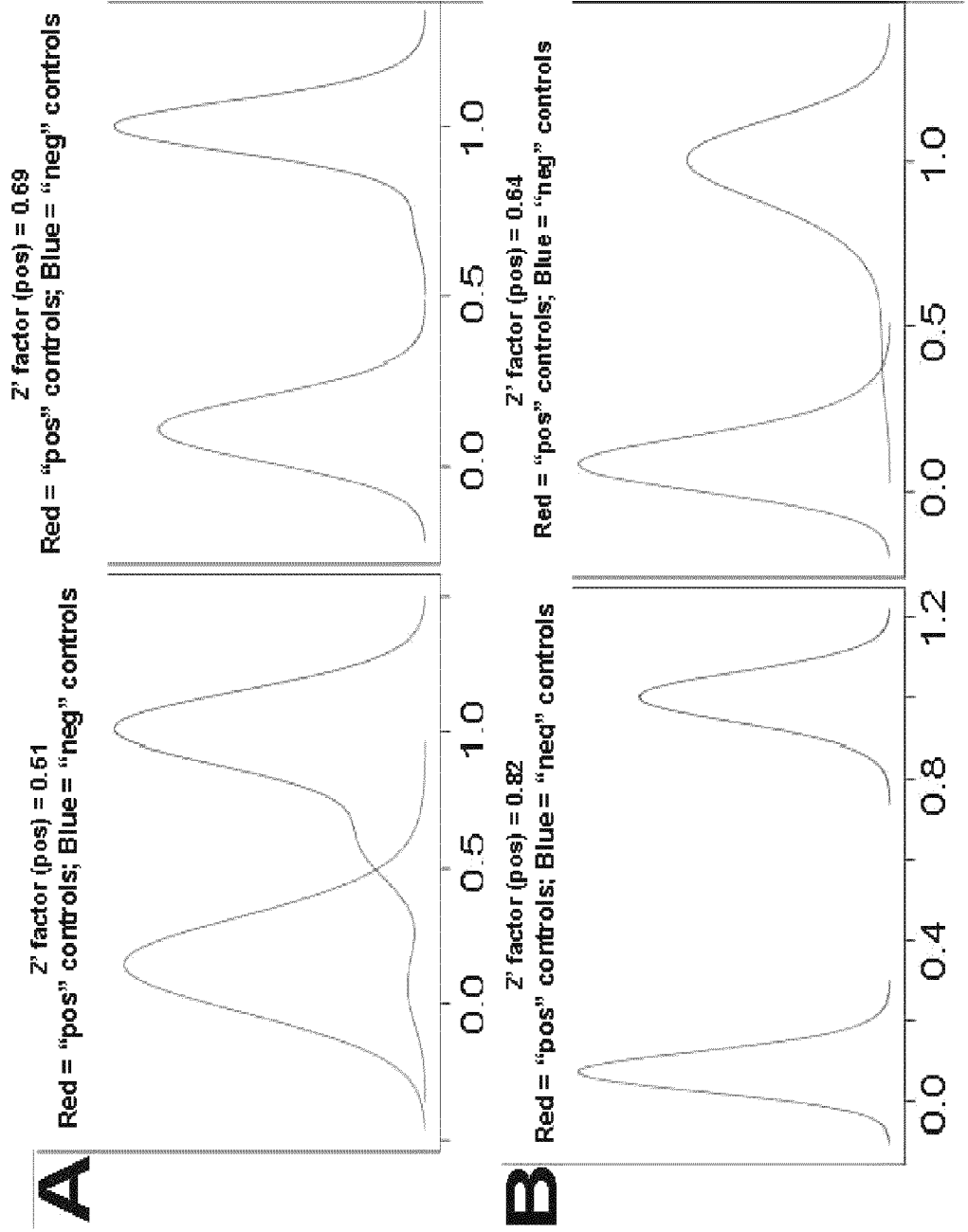
FIG. 2 shows normalized intensities of individual readings of the positive (right peak) and negative (left peak) siRNA controls as shown in FIG. 1. Duplicates (left and right) were treated with vehicle (A) or gemcitabine (B). Z-scores were all >0.5.

The screen was conducted in 384 well plates where 300 siRNAs from the library (Dharmacon SMARTpool of approximately 23,000 siRNAs) were tested on each plate (FIG. 1). Killer (positive) and non-killer (negative) control siRNAs were plated in a checkered board fashion in the remaining 84 wells to control for transfection efficiency, edge effects, and pipetting errors. Optimization efforts made a difference as seen by high z-scores (>0.6), a statistical value that is used to evaluate the quality of HTS data. Z-scores of <0.5 means there is low confidence in the data points and a screen has to be repeated. Z-scores of >0.5 validate any differences in data points between drug and no drug treatment. Duplicate plates were treated with vehicle or a sublethal dose gemcitabine (4×384 plates/300 siRNAs) for 24 hours and viability quantitated with CellTiter-Glo® (Promega Corp., Madison, Wis.). FIG. 2 shows the wide dynamic range and reproducibility between positive and negative siRNA controls after treatment with vehicle or gemcitabine.

In addition to the z-score, the false discovery rate (FDR) was also calculated for each siRNA. FDR is a statistical method used to reduce false positives in screens that rely on comparison between different treatment conditions (+/−gemcitabine). The FDR threshold is ascertained from the observed P value distribution and is adaptive to the differences in the signal level in our data from experiment to experiment. FDR values between 0.0 to 0.2 indicate that the difference in the readouts between drug and control treatments is significant.

Using stringent z-scores (>0.6) and false discovery rates (FDR's between 0 to 0.2), 125 primary candidates were further tested for gemcitabine sensitization with an independent set of siRNAs. Twenty seven genes were validated, and ~50% were grouped into functional networks by Ingenuity and String (not all hits were assigned to a network). One group comprised DNA damage responders and cell cycle regulators (ERCC1, Chk1, PIAS4, Wee1, and 53BP1) that are known to sensitize cell killing by gemcitabine and other cytotoxic agents. This finding independently validated the screening strategy and raised confidence in other candidates. The second group belonged to the VDR transcription network that included VDR, and associated transcription factors RXRa, RUNX2 and ZBTB16, as well as known transcriptional targets such as CYP2B6 and ABCB1 (MDR1). Notably, CYP2B6 and ABCB1 encode cytochrome P450 and the ABCB1 (MDR1) multidrug resistance transporter, that are directly responsible for eliminating drugs from cells. Amongst the 27 validated sensitizers, 6 had consensus VDRE's (VDR, BCKDHB, CGI-63, STK39, 53BP1, IL13RA1). Furthermore, MMP13 was a validated hit that is a known target of RUNX2

The VDR is a nuclear hormone receptor family member that binds vitamin D and plays an essential role in calcium homeostasis and mineralization of bone. In addition, it acts in diverse biological pathways that are important for immune functions, cell differentiation, and growth control. Vitamin D and the VDR are considered as targets for cancer therapy as vitamin D has anti-proliferative activity against a variety of cancer cells in vitro (Moffatt K A et al. (1999) Clin. Cancer Res. 5:695-703; Krishnan A V et al. (2007) J. Bone Miner. Res. 22 Suppl 2:V74-80), in vivo (Hershberger P A et al. (2001) Clin. Cancer Res. 7:1043-51; Zhang X et al. (2005) Clin. Cancer Res. 11:323-8; McElwain M C et al. (1997) Am. J. Otolaryngol. 18:293-8; Getzenberg R H et al. (1997) Urology 50:999-1006) and in clinical trials (Beer T M (2007) J. Clin. Oncol. 25:669-74; Trump D L (2006) Cancer 106:2136-42).

That the VDR knockdown would enhance sensitization to gemcitabine was unexpected. Nevertheless, reports that VDR expression was induced by DNA damage prompted further pursuit. It was reasoned that genome instability that is inherent to pancreatic cancer cells might constitutively activate cell survival and anti-apoptotic pathways. Such a heightened state may explain in part their ability to survive extrinsic genotoxic stresses. To validate the results, a VDR short hairpin RNA (clone ID TRCN000019504) was used whose sequence was different from the library siRNAs. This shRNA had the sequence CGAAGUGUUUGGCAAUGAGAU (SEQ ID NO: 7), and was tested on both Panc1 and BXPC3 cells, the latter of which is a pancreatic adenocarcinoma.

Figure 3A:
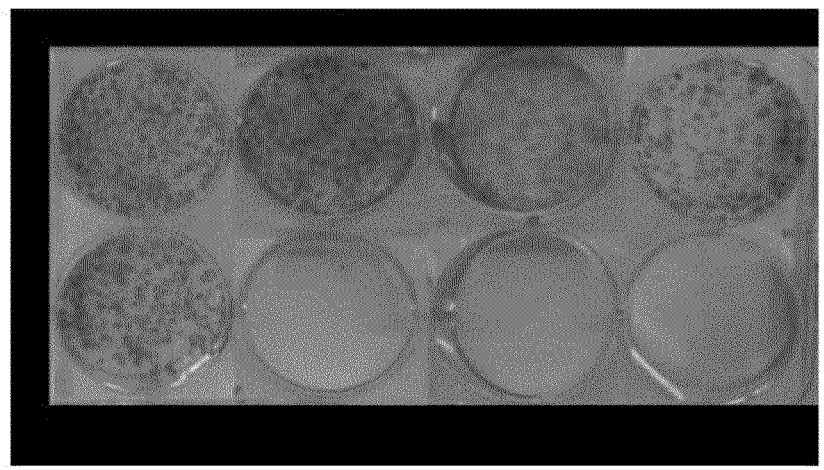
FIG. 3A shows survival of cells transfected with VDR siRNA or Chk1 siRNA and treated for 18 hours with gemcitabine.

CellTiter-Glo® viability assay confirmed that VDR knockdown sensitized both cell lines to killing by gemcitabine. Cells were transfected with siRNA, treated with gemcitabine for 18 hours, then seeded. Surviving colonies were quantitated eight days later. Depletion of VDR reduced the clonogenic survival of Panc1 and BXPC3 cells (FIG. 3A). VDR siRNA alone reduced colony formation by ~15% compared to control, and is believed to be attributed to intrinsic genotoxic stress. Gemcitabine further reduced survival by >85% for both Panc 1 and BXPC3 cells. Sensitization was comparable to knockdown of the Chk1 DNA damage checkpoint kinase.

Figure 3B:
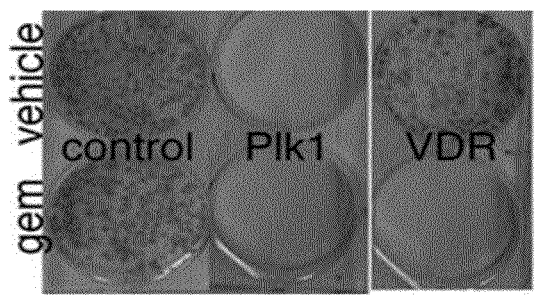
FIG. 3B shows VDR siRNA enhance gemcitabine sensitivity. Clonogenic survival of BXPC3 cells transfected with indicated siRNAs and treated with drug or vehicle. Plk1 siRNA is positive control for killing.
Figure 3C:
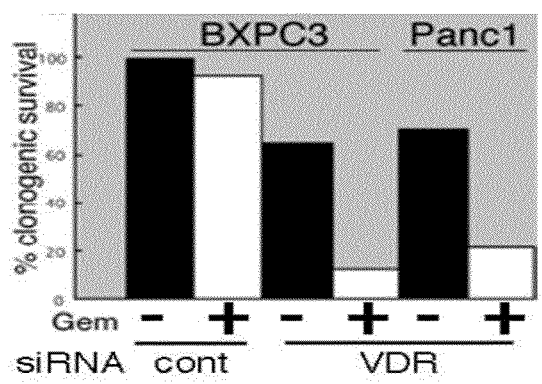
FIG. 3C shows quantitation of the clonogenic data. Panc 1 cells transfected with VDR siRNA are also included.

These results were extended by performing clonogenic assays with a sublethal dose of gemcitabine (FIG. 3B & FIG. 3C). Cells were transfected with siRNA and gemcitabine was added 36 h later. Drug was removed 12 hours after addition, and cells were re-plated for colony formation. After 8 days, control siRNA showed no difference between vehicle and gemcitabine. VDR siRNA reduced colony formation in vehicle treated cells by ~33% when compared to control siRNA. Reduced colony formation may potentially due to intrinsic genotoxic stress as a result of genome instability. However, colony formation was further reduced by >80% in the presence of gemcitabine. Similar sensitization was also seen with Panc 1 cells. The clonogenic results therefore validated the sensitization data obtained from the primary screen.

Figure 4A:
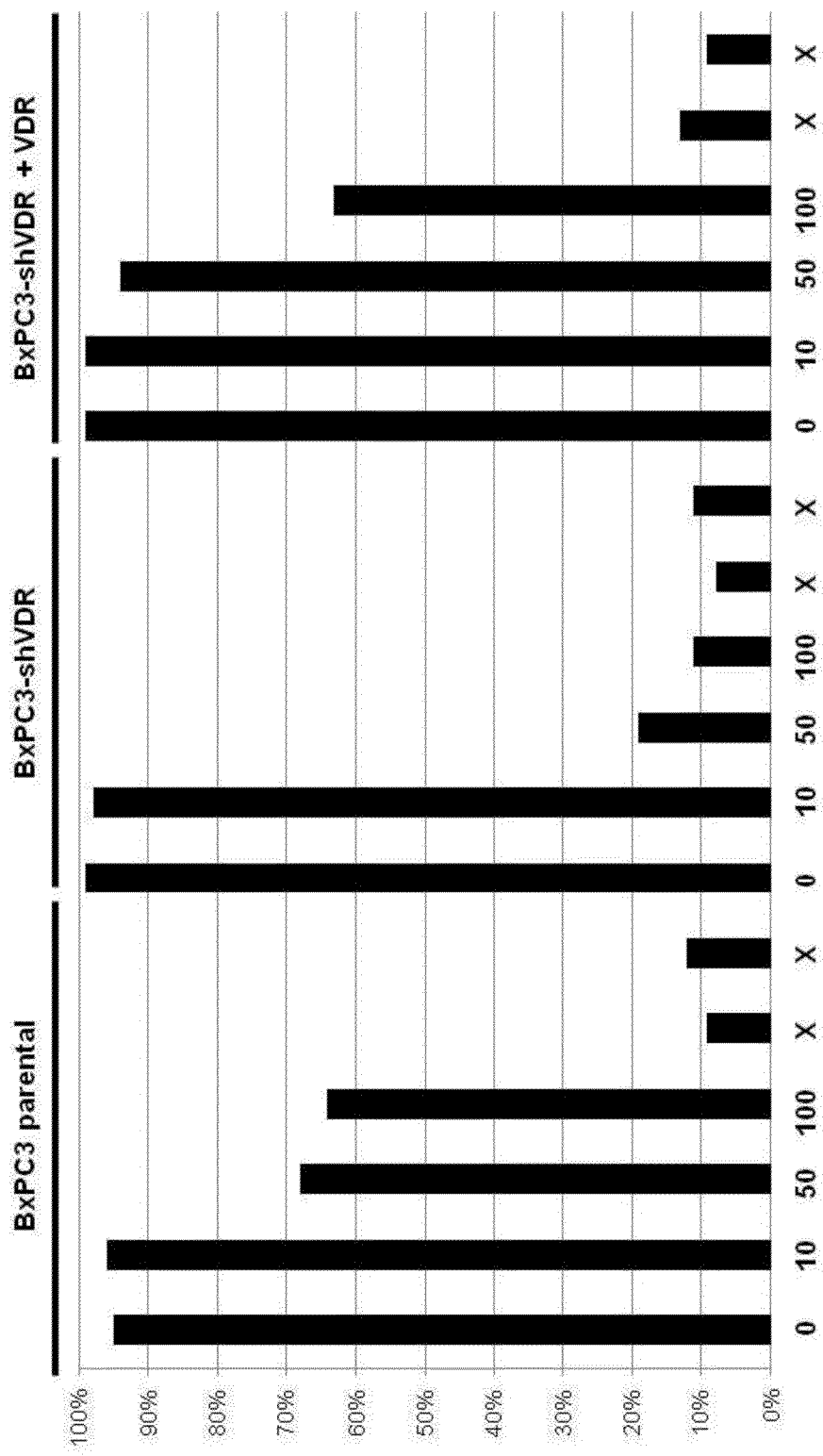
FIG. 4A shows BXPC3 stably depleted of VDR (−sh-VDR), transfected with RNAi VDR (+VDR), and tested for gemcitabine sensitivity relative to BXPC3 parental cells: surviving colonies (y axis), gemcitabine ($\mu$M) (x axis); x designates two different concentrations of taxol. Data represents the average of 3 independent experiments.

Additional experiments evaluated whether gemcitabine survival could be rescued with wild type VDR. A BXPC3 cell line in which the VDR was stably knocked down by inserting a shVDR into its genome (BXPC3shVDR). An RNAi-resistant allele of VDR was found to restore gemcitabine survival in BXPC3 cells stably depleted of VDR (<10% by blots, data not shown)(FIG. 4A). VDR status did not affect killing by two concentrations of taxol (lanes x), which targets microtubules.

Figure 4B:
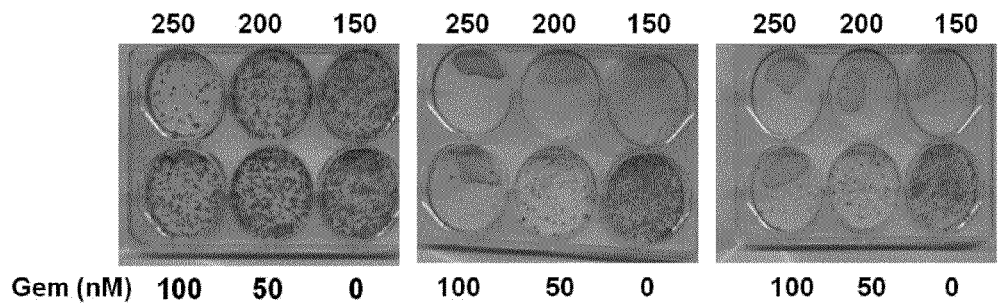
FIG. 4B shows ligand binding and heterodimerization domains of VDR are essential for BXPC3 cells to survive gemcitabine.
Figure 4C:
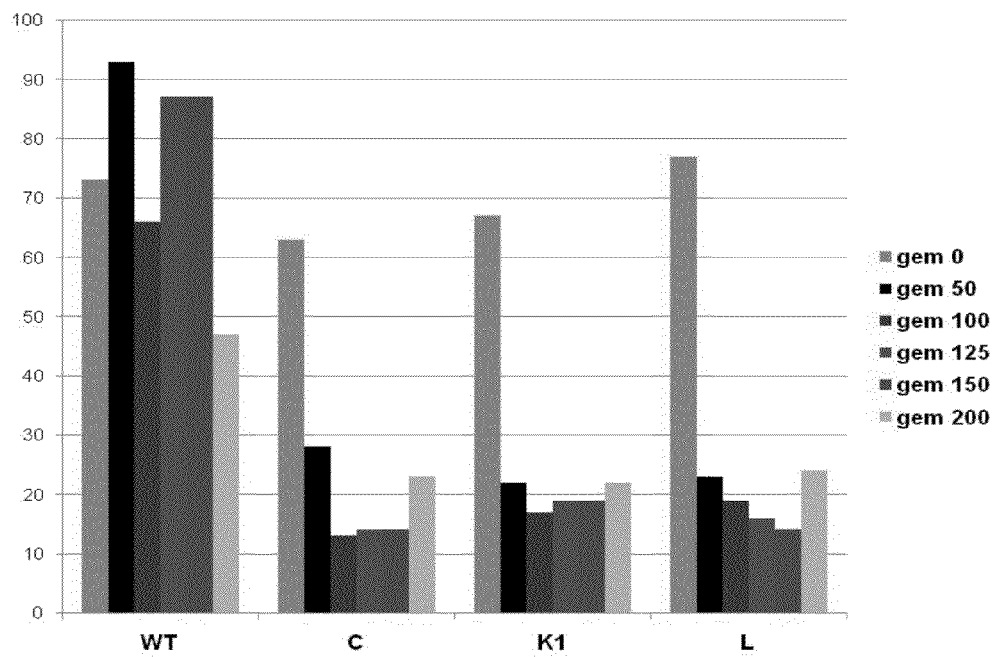
FIG. 4C shows survival as a function of the amount of gemcitabine ($\mu$M). The mutant designated C has the mutation C to G at position 288 within the VDR cDNA which renders the mutant defective in ligand-binding and transactivation functions of VDR. Mutant K1 has the mutation K to G at position 246 that renders VDR defective in its transactivation functions. Mutant L has the mutation L to G at position 254 that also renders VDR defective in its transactivation functions.

In addition, two mutants of VDR were screened to confirm the role of VDR in gemcitabine resistance by determining if either or both mutant could rescue gemcitabine survival. The first mutant, C288G, is known to be unable to bind to the Vitamin D ligand, which is essential for the ability of the VDR to promote transcription of its target genes. The C288G mutant failed to rescue BXPC3shVDR cells (killed at 50 nM, compared to the same cells rescued by the wild type VDR) (FIG. 4B and FIG. 4C). The second mutant, L254G, is unable to transactivate VDR target genes. The L254G mutant also failed to rescue BXPC3shVDR cells (FIG. 4B and FIG. 4C). These data provide molecular evidence that the survival functions specified by VDR depend on ligand binding and transactivating its target genes.

Figure 5A:
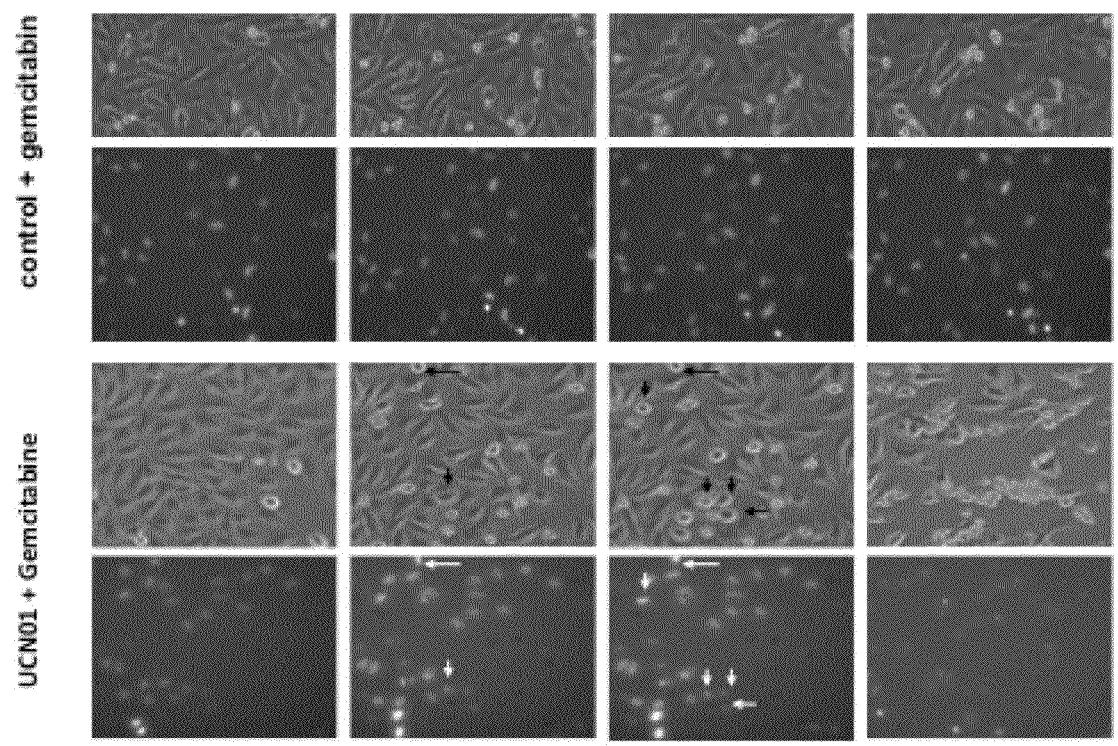
FIGS. 5A-5C show time lapse videomicroscopy tracking the fates of Panc1:gfpH2B cells treated with various combinations of siRNAs and drugs.

The fate of Panc1:gfpH2B cells treated with various combinations of siRNA and gemcitabine was tracked with time-lapse videomicroscopy (FIG. 5A). In FIG. 5A, the top row for each data set shows phase contrast images that identify cells, and the bottom row shows the fluorescence image from gfpH2B marking the chromatin and chromosome of the cells shown in the top row. Cells were transfected with indicated siRNAs, and synchronized at the G1/S boundary. Time-lapse was started upon release from the G1/S block and continued for the next 48 hours. Select frames from the movies (0, 12, 24 and 48 hours) are shown.

A comparison of cells treated with gemcitabine in the presence and absence of UCN01, an inhibitor of the Chk1 DNA damage response kinase was carried out (FIG. 5A). Phase contrast images at 0 and 48 hour time points show reduced cell number after UCN01 treatment. The fluorescence channel showed that UCN01 treatment promoted cells to first enter mitosis (arrows) which then caused cell death.

Figure 5B:
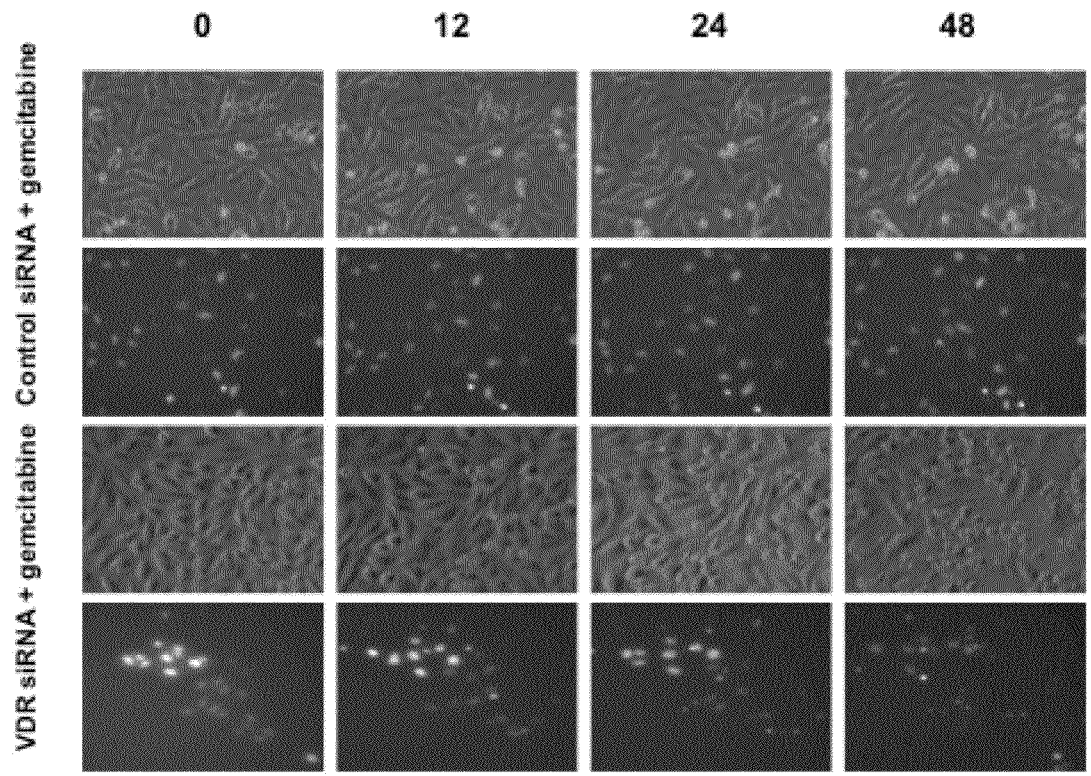
Figure 5C:
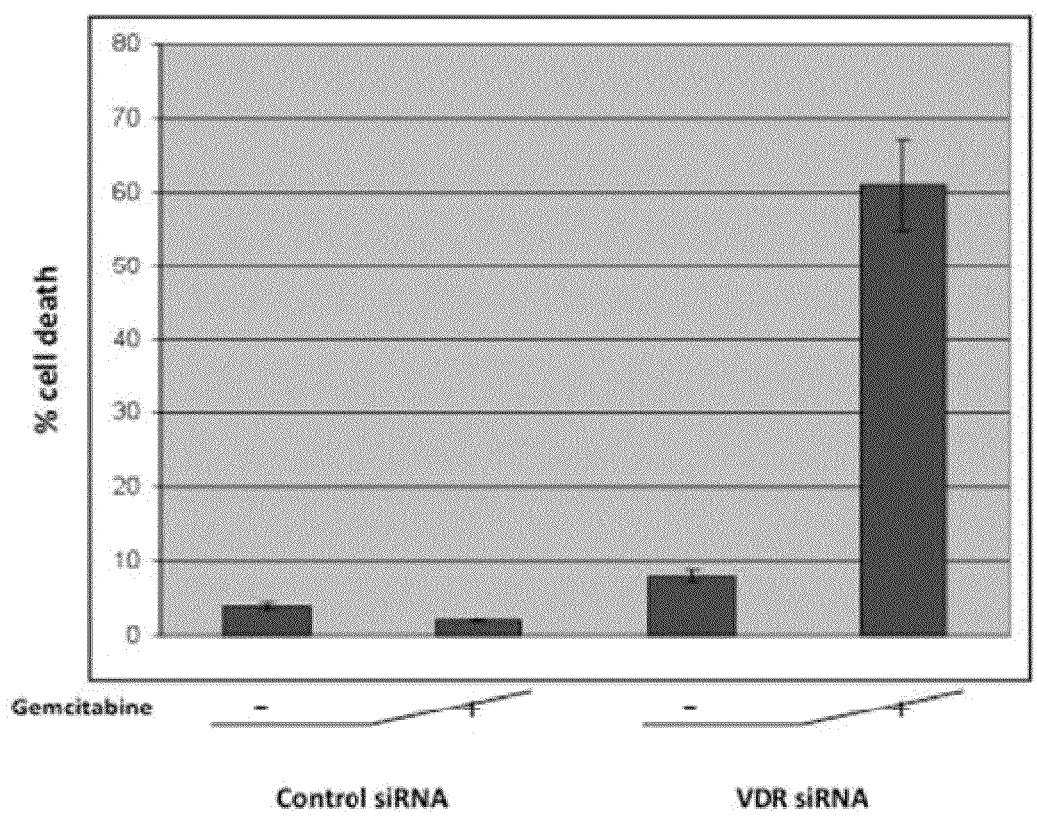

Images of cells transfected with control or VDR siRNA and treated with gemcitabine were also taken, as shown in FIG. 5B. A comparison of the 0 and 48 hour time points shows the presence of apoptotic cells in the VDR siRNA-treated samples at 48 hours. The percentage of cell death was quantified (FIG. 5C).

Example 4

Role of VDR Targets in Gemcitabine Sensitization

Figure 6A:
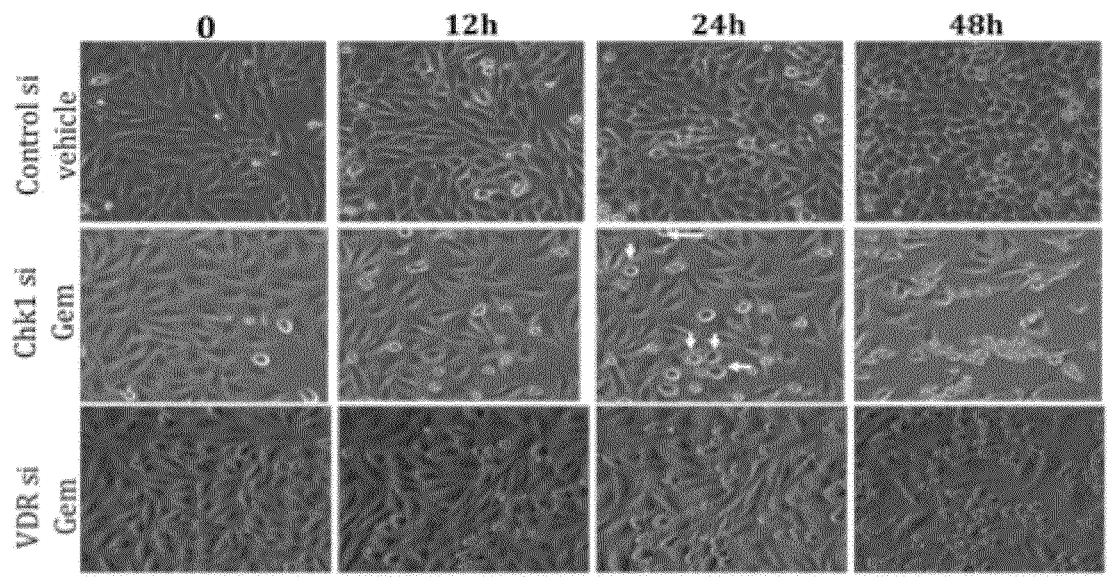
FIG. 6A shows phase images from select frames of a 48 hour time-lapse of Panc1 cells treated as indicated (left). White arrows show mitotic cells in Chk1 depleted cells. Other rounded cells are apoptotic.
Figure 6B:
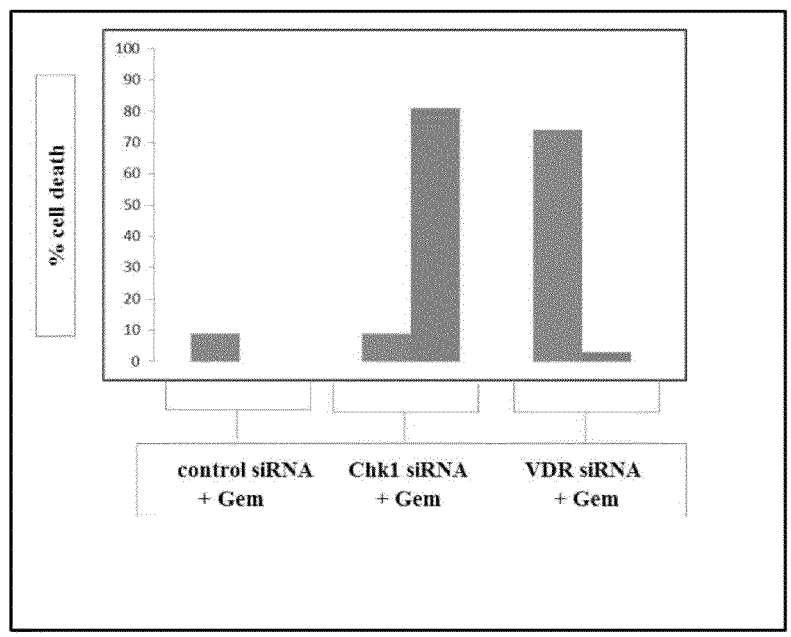
FIG. 6B shows quantitation of time lapse studies, and that Chk1 siRNA kills cells in mitosis while CDR depletion kills cells in interphase.

The mechanism of chemosensitization by inhibiting VDR was investigated, and it was determined that this mechanism is different from overriding the DNA damage checkpoint pathway through Chk1 inhibition (FIG. 6A). Time lapse studies clearly showed that depletion of Chk1 from gemcitabine-treated cells caused premature mitotic entry (white arrows in 24 h panel), where many of them died after 4-6 hours (FIG. 6B, right bar). Chk1 was depleted by using siRNAs targeted to the Chk1 transcript from the Dharmacon smartPOOL siRNA library. The siRNAs included the sequence GCAA-CAGUAUUUCGGUAUA (SEQ ID NO:8), GGACUUCU-CUCCAGUAAAC (SEQ ID NO:9), AAAGAUAGAUG- GUACAACA (SEQ ID NO:10), and AGAUAUGAAGCGUGCCGUA (SEQ ID NO:11).

For VDR-depleted cells that were treated with gemcitabine, no cells entered mitosis, but instead died while arrested in S phase (FIG. 6B, left bar) within 16 hours of gemcitabine treatment. Loss of VDR promotes apoptosis of gemcitabine-treated cells through a different pathway than that which is used after Chk1 inhibition.

A connection between VDR and the DNA damage response pathway was identified. Phospho-H2AX and 53BP1 staining were increased in nuclei of gemcitabine-treated cells compared to vehicle treated cells. In cells depleted of VDR, phospho-H2AX and 53BP1 failed to accumulate in nuclei after gemcitabine treatment (FIG. 7A). 53BP1 was a validated hit from the screening assay and indeed, inspection of its promoter revealed a consensus VDRE, the recognition site for VDR.

The VDR is essential for recruitment of the p53-binding protein 1 (53BP1) (a DNA damage response protein), to sites of damage in cells treated with gemcitabine. Immunofluorescence staining for DNA damage response proteins, TAO1, 53BP1, and γ-H2AX of gemcitabine treated Panc1 cells transfected with control or VDR siRNA. In control cells, TAO1, 53BP1, and γ-H2AX localize to nucleus at sites of DNA damage that appear as punctate foci. VDR siRNA reduces the levels of these proteins within the nucleus at sites of DNA damage.

Figure 7A:
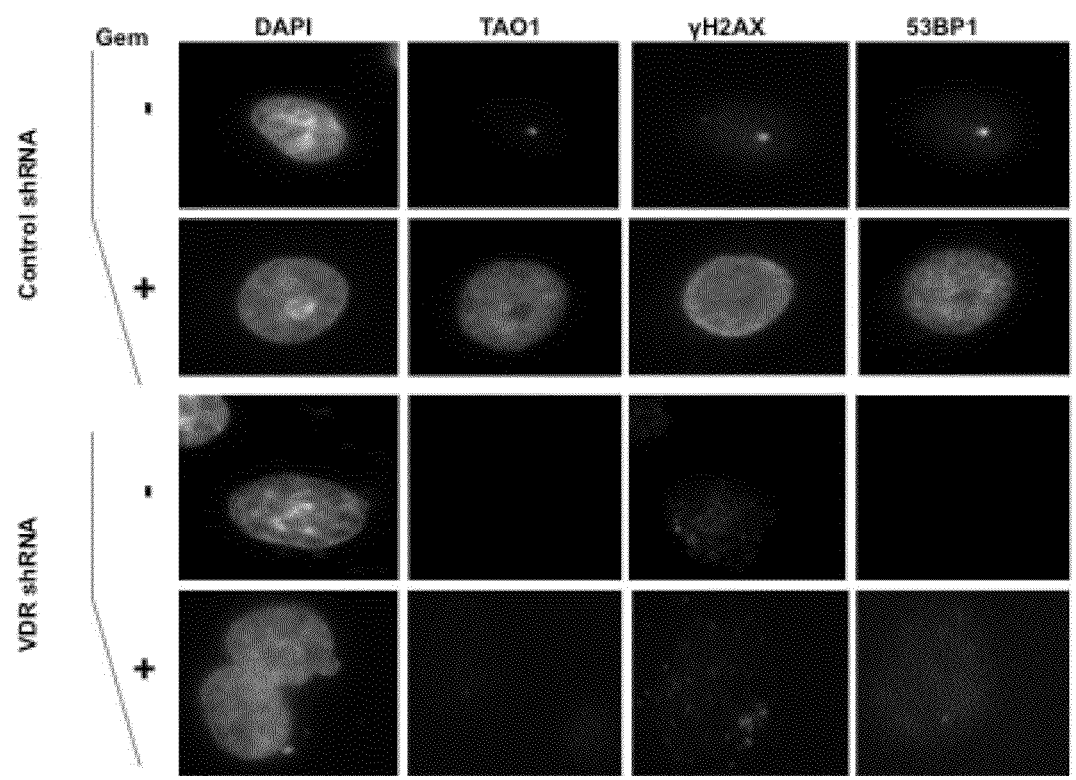
FIG. 7A shows immunofluorescence staining of Panc1 cells transfected with the indicated siRNA (VDR or control), and stained for DAPI, TAO1, γH2AX, and 53BP1 after 16 hours of gemcitabine treatment.
Figure 7B:
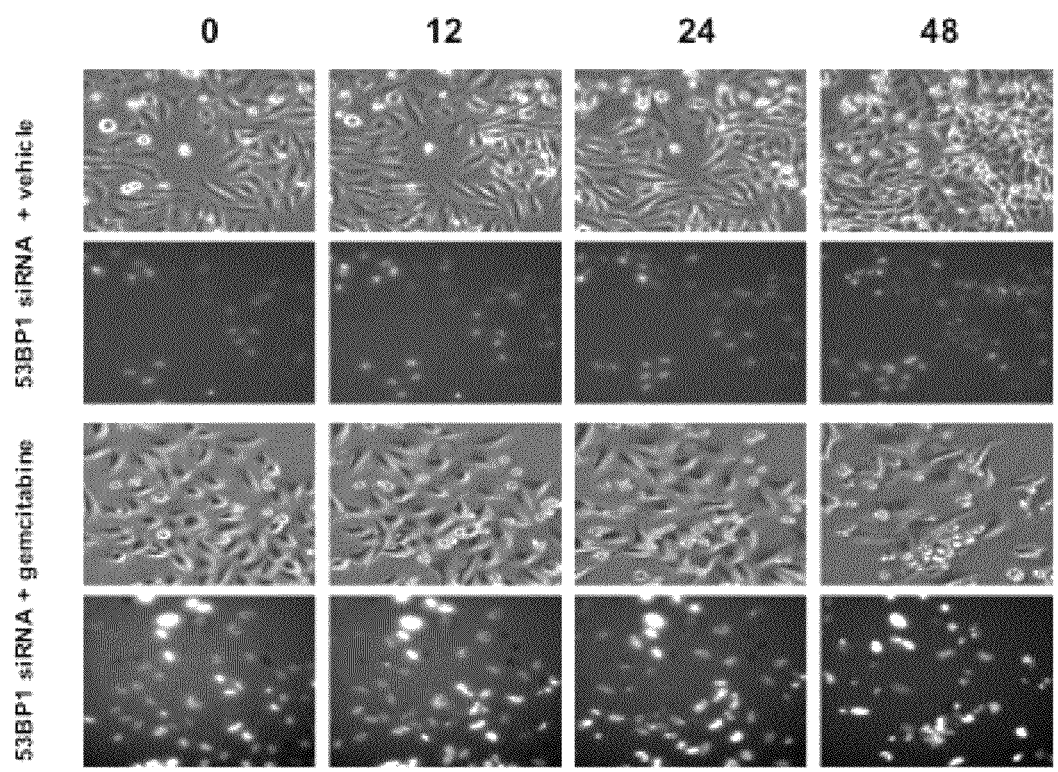
FIG. 7B shows that 53BP1 ablation mimics VDR sensitization independent of Chk1 override.

Time lapse studies showed that 53BP1 Dharmacon siRNA pools (depletion of 53BP1) killed gemcitabine arrested Panc1:gfpH2B cells in S phase, as was shown for VDR siRNA (FIG. 7B). The target sequences were GAGAGCAGAUGAUCCUUUA (SEQ ID NO:12), GGACAAGUCUCUCAGCUAU (SEQ ID NO:13), GAUAUCAGCUUAGACAAUU (SEQ ID NO:14), and GGACAGAACCCGCAGAUUU (SEQ ID NO:15). There was no evidence that depletion of 53BP1 caused cells to prematurely enter mitosis, as when Chk1 was inhibited. The response of 53BP1-depleted cells to gemcitabine is similar to depletion of VDR (compare FIG. 5B). This provides a further functional connection between VDR and 53BP1 in promoting survival in response to gemcitabine.

Figure 8A:
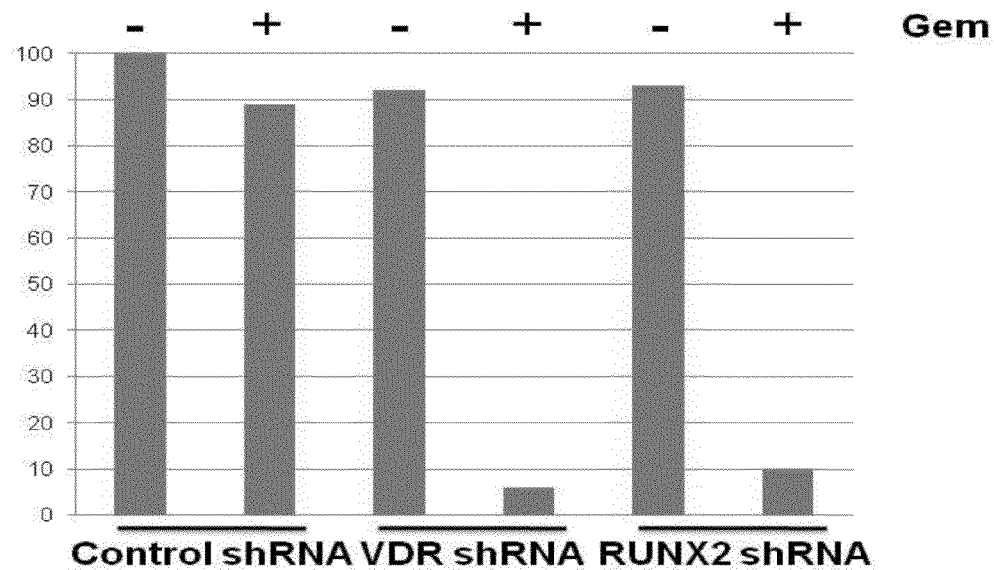
FIG. 8A shows that RUNX2 depletion sensitizes pancreatic cancer cells to killing by gemcitabine. Clonogenic assay was performed on Panc1 cells that were transfected with control, VDR, and RUNX2 shRNAs. Cells were treated with vehicle or gemcitabine for 24 hours before they were re-plated for clonogenic assay. Surviving colonies after 7-10 days were fixed and stained (left) and counted and compared (right).
Figure 8A:
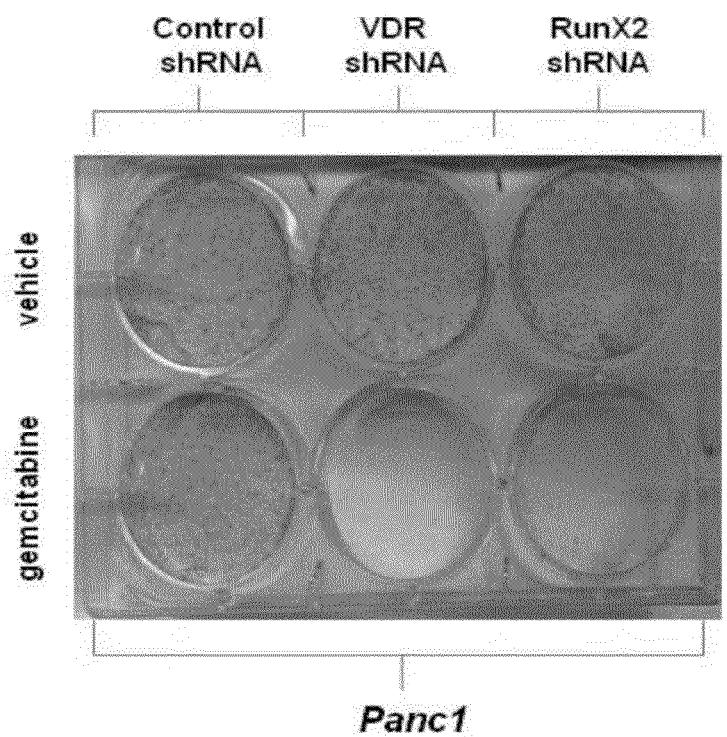
Figure 8B:
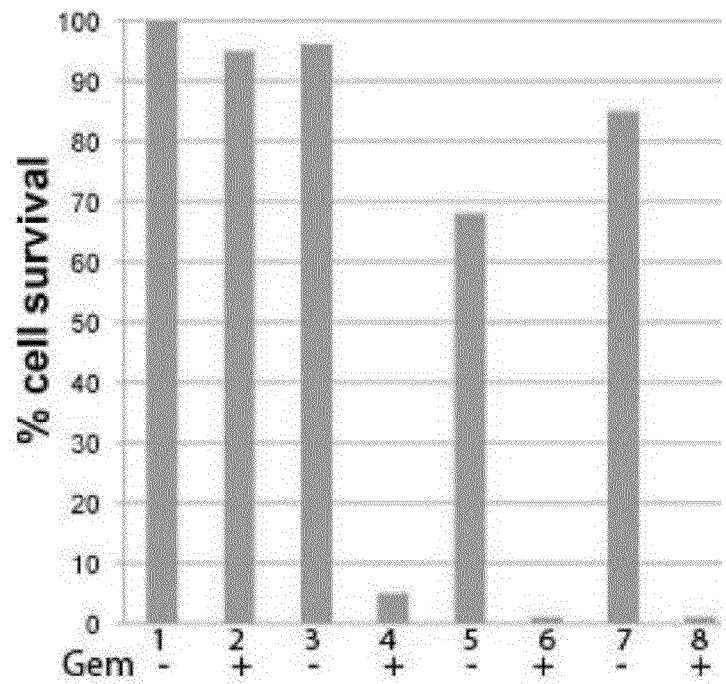
FIG. 8B shows surviving colonies of Panc1 cells depleted of Chk1, RUNX2, and VDR after 24 h of vehicle (−) or gemcitabine (+) treatment. The average of 3 independent experiments is shown.

Depletion of RUNX2, a transcription factor that co-regulates a subset of VDR genes, sensitized pancreatic cancer cells to killing by gemcitabine. A clonogenic assay was performed on Panc1 cells that were transfected with control, VDR, and RUNX2 shRNAs. The target sequence for the RUNX2 target was GCUACCUAUCACAGAGCAAUU (SEQ ID NO:16). Cells were treated with vehicle or gemcitabine for 24 hours before they were re-plated for the clonogenic assay. As shown in FIG. 8A, surviving colonies after 7-10 days were fixed and stained (left) and counted and compared (right). It was determined that knockdown of RUNX2 sensitized Panc1 cells to gemcitabine equally effectively compared to knockdown of VDR or Chk1 (FIG. 8B).

Based on these experiments, additional studies will be undertaken to understand how the VDR promotes survival of cells to gemcitabine, including studies to identify its transcriptional targets. This is useful at two levels—knowing target genes that are responsible for survival will expand the targets for drug sensitization, and these genes can be biomarkers for VDR activity in both research and clinical settings.

The experiments will focus on the validated sensitizers genes (VDR, BCKDHB, CGI-63, STK39, 53BP1, IL13RA1) identified from the initial screen that contain consensus VDRE's within their promoter (<500 bp from the transcription start site). 53BP1 is one such candidate target gene whose protein product failed to localize at DNA damage foci upon depletion of VDR (FIG. 7A).

Consensus RUNX2 binding elements have been identified in the promoters of the validated genes (e.g., MMP13), some of which also contain VDRE's (data not shown). The osteopontin gene, which is essential for osteoblast differentiation, is activated by the cooperative binding of VDR and RUNX2 to its promoter. Thus, gemcitabine survival of pancreatic cancer cells may rely on genes that are co-stimulated by RUNX2 and VDR.

Chromatin immunoprecipitation (ChIP) will be used to directly test the occupancy of VDR and RUNX2 in promoters of the validated genes. BXPC3 cells+/−VDR will be treated with gemcitabine for 4 and 12 hours (when DNA damage is maximally detected) and then treated with formaldehyde to crosslink proteins to DNA. After quenching, cells will be lysed, and the chromatin fraction sonicated and the supernatants subject to ChIP, using VDR, RUNX2 (ChIP grade commercial antibodies) and non-immune IgG. The antibody complexes are isolated and after reversal of crosslinks, the DNA fragments are purified and subject to PCR using overlapping primers pairs that span every 250 bp within 1 kb of the transcription start.

It is believed that fragments containing the VDRE will be enriched in the VDR ChIPs. VDR is known to bind to the osteopontin promoter in U20S cells and this can be used to confirm the ChIP. The promoter for MMP13 metallopeptidase, which is one of the validated sensitizers, will be the positive control for RUNX2 ChIP. Naked genomic DNA from BXPC3 cells will provide positive controls for all the PCR primer pairs. The VDR knockdown cells will provide an additional negative control for non-specific ChIP signal. If stable RUNX2 knockdown cells are isolated, it will also provide an additional negative control for the RUNX2 ChIPs.

In parallel with the ChIP experiments, the expression of the candidate VDR and RUNX2 target genes will be compared by real-time PCR. It is believed that gemcitabine upregulates genes that are directly regulated by VDR or RUNX2. RNA will be isolated from the BXPC3+/−VDR cells (or TEI-9647 can be used as an alternative way to inhibit VDR) at different times after gemcitabine treatment (0, 4, 12, 24 h), and will be processed for qRT-PCR.

PCR products from VDR and RUNX2 ChIPs, but not for non-immune IgG, or the knockdown cells, will confirm that the promoter regions are direct targets. The ChIP experiments will reveal how many of the validate sensitizers are direct targets of VDR, RUNX2 or both. Depending on the p53 knockdown outcome (see Examples below), mutant p53 can be tested to determine if p53 occupies promoters that also bind VDR. If drug treatment enhances promoter binding, it is expect that a stronger PCR product will be produced relative to vehicle treated samples. This should be reflected in increased expression of the mRNA as determined by qRT-PCR. It is possible that the promoters are already occupied by VDR and RUNX2 under normal conditions owing to the intrinsic stress that the cells are under. However, the mRNA expression levels may still increase after gemcitabine treatment. If PCR products are not detected from a ChIP, it would suggest that the gene is not a direct target, or the time point was not optimal for that gene. The qRT-PCR studies should provide better temporal information about the expression patterns of the candidate target genes as a function of gemcitabine treatment. If the mRNA expression is elevated despite the lack of promoter occupancy by VDR or RUNX2, it would suggest that these transcription factors are not directly responsible for its expression.

As a next step, VDR and RUNX2 levels will be evaluated in patient tumor samples by immunohistochemistry. Pancreatic adenocarcinoma samples collected from patients who underwent surgical intervention at Fox Chase Cancer Center and consented to the collection, and for which the IRB approved to have the tumor stored for future research, will be used. Approximately 100 formalin-fixed, paraffin-embedded (FFPE) samples are currently available from the FCCC Biosample Repository. All of the samples have well annotated clinical information that include demographics, treatment and survival data (all died within 2 years after diagnosis), that are available through the tumor registry. Samples will include patients who received neoadjuvant chemoradiotherapy and patients who were resected for cure prior to any adjuvant gemcitabine-based treatment (100% surgery+chemo follow-up). In addition, histopathological staging based on AJCC TMN scores are available for all tumors. A set of TMAs has already been constructed from 39 pancreatic cancers (29-adenocarcinoma, 7-infiltrating ductal carcinoma, and 3-mucinous adenocarcinoma), along with 10 normal pancreas and other organs.

Commercially available anti-VDR and RUNX2 antibodies that have been validated for immunohistochemistry in patient tissue samples will be used. Samples will be deparaffinized by xylene, rinsed in ethanol, and rehydrated in water and PBS. For antigen retrieval, slides will be steamed in DAKO Target Retrieval solution, cooled, washed in PBS. After peroxidase blocking, slides will separately incubated with primary antibody overnight (VDR and RUNX2). Staining will be scored in a blinded manner, and based on intensity of staining relative to internal and external controls, and graded 0 to 2. The percentage of cells that are stained within the each field will be classified as <10%, 10-50%, and >50%, (scale: 0, 1, 2) along with distribution of staining within the tissue section. Although nuclear staining for VDR and RUNX2 is expected, cytoplasmic staining will also be scored if it is detected.

For statistical analysis, the Spearman rank correlation and its 95% confidence interval (CI) between biomarker (VDR, RUNX2) and T stage will be calculated. The strength of correlation (rho) will be classified as strong, moderate and weak for the correlation coefficient>0.8, 0.4-0.8, and <0.4 respectively. Biomarkers will be considered correlated with T stage if the 95% CI does not cross zero. VDR and RUNX2 scores will be further dichotomized into low (0 and 1) and high (2). T scores will also be separated between low (T1, 2) and high (T3 and T4).

Example 5

Small Molecule VDR Antagonists Sensitize Cells to Gemcitabine

Figure 9:
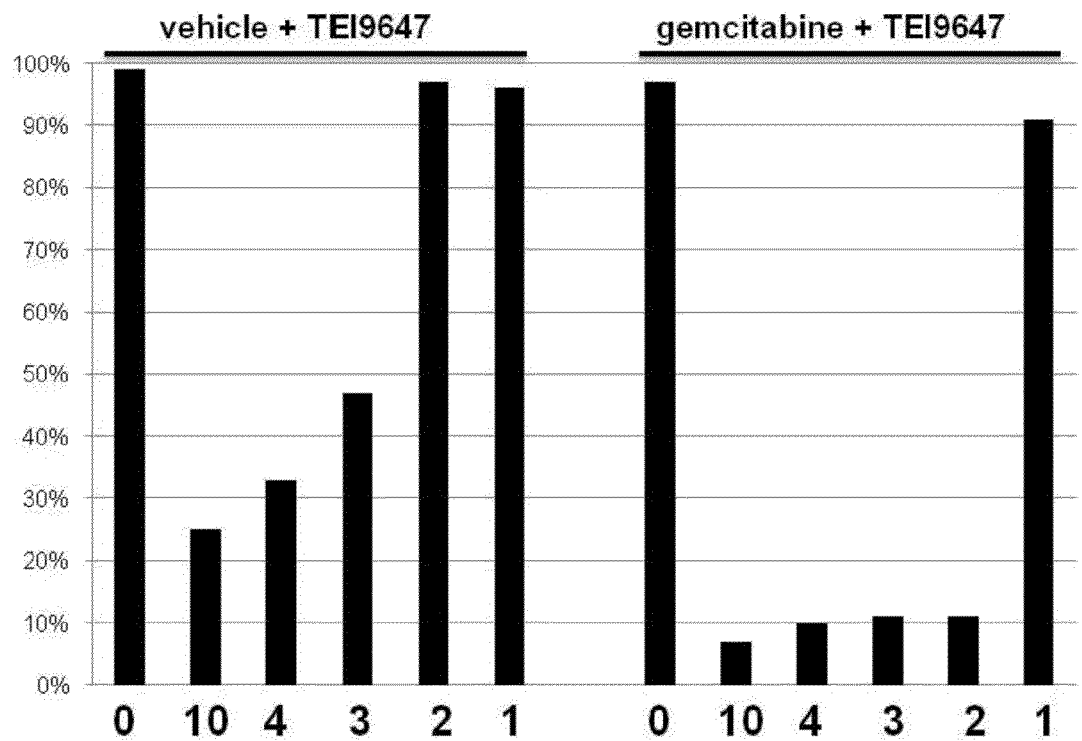
FIG. 9 shows BXPC3 cells were treated 24 h with TEI-9647 alone (left) or with gemcitabine (right) and plated for surviving colonies (y-axis); TEI-9647 (μM) (x axis). Note sensitization at 2 μM of TEI-9647. The average of 3 independent experiments is shown.

A small molecule VDR antagonist, TEI-9647, was found to sensitize both BXPC3 and Panc1 cells to gemcitabine (FIG. 9, Panc1 not shown). TEI-9647 alone killed cells, consistent with reduced clonogenic survival by VDR siRNA alone. Clonogenic assays were performed using several different doses of the inhibitor compound to compare clonogenic survival to assays described above using VDR siRNAs and shRNAs. The clonogenic assays were performed as described above. The TEI-9647 compound was added prior to gemcitabine addition, consistent with the timing of the siRNA treatments described above. Cells were treated with inhibitor for 48 hours followed by gemcitabine treatment for 48 hours and allowed to form colonies for 10-12 days. Survival was then quantified by staining and destaining of subsequent colonies with crystal violet and reading the resultant destain at wavelength 595 nm.

Example 6

Mechanism for VDR Contribution to Clonogenic Survival of Gemcitabine-Treated Cells Bioinformatic analysis of the top 125 hits identified several candidates that act with or lie downstream of the VDR. RXR, RUNX2 and ZBTB16 are transcription factors that are known to interact with VDR. These proteins may together or independently target the VDR pathway genes to promote survival in response to gemcitabine. As shown above, knockdown of RUNX2 renders cells more susceptible to gemcitabine. In addition, VDR mutants that implicate a role for RXR suggest that knockdown of RXR will render cells more susceptible to gemcitabine. As well, it is believed that knockdown of ZBTB16 may effectively result in a VDR-deficient state that renders cells more susceptible for gemcitabine. siRNAs RXR and ZBTB16 will be tested for sensitivity of cells to gemcitabine as with VDR. If these targets are validated, their expression profiles will be compared using microarray to identify overlapping genes that may specify gemcitabine sensitivity.

CYP2B6, a member of the cytochrome P450 family of enzymes that are responsible for drug metabolism, was also identified from the screen. CYP2B6 is of interest because it is transcriptionally activated by the VDR and other steroid hormone receptor family members. Although its accepted role in drug metabolism suggests an obvious connection with gemcitabine sensitization, there is accumulating evidence that CYPB26 plays a role in energy metabolism and cellular homeostasis. These latter functions may be important for cancer cells to maintain their "transformed state" that include response to cytotoxic agents. These, along with the fact that it is a downstream target of the VDR are reasons to validate the CYP2B6 knockdown.

The validation experiments will include rescue with RNAi-resistant alleles of the targets. Additional pancreatic adenocarcinomas such as MiaPaca2, CF-PAC, and HPAFII will be tested to see if the VDR pathway(s) is a common feature of pancreatic cancer cells. Positive outcomes from the validation experiments will lead to the testing of existing chemical inhibitors of VDR (vitamin D antagonists), or cytochrome P450. The availability of drugs may facilitate future xenograft studies and clinical trials.

A relevant question to investigate is how does VDR knockdown sensitize cells to killing by gemcitabine? Gemcitabine arrests cells in S phase as a result of activation of the DNA damage checkpoint. ATM and Chk1 kinases are components of the checkpoint arrest and inhibitors have been shown to enhance killing drug treated cells. The importance of the checkpoint is underscored by the fact that tumors in patients may use this as a mechanism to maintain viability until the drug is metabolized. Overriding the checkpoint arrest may cause cells to undergo mitotic catastrophe.

VDR is known to induce transcription of the Cdk inhibitor, p21, and this is one of the reasons used to explain the antiproliferative activity of vitamin D. As p21 is also activated by DNA damage, it is possible that VDR contributes to the cell cycle checkpoint arrest induced by gemcitabine. This will be directly tested by time-lapse microscopy of synchronized cells after depletion of VDR and treatment with gemcitabine. Preliminary experiments show that BXPC3 cells stably expressing gfpH2B can remain arrested for up to 48 hours in interphase (S phase by FACS) after gemcitabine treatment.

However, Chk1 siRNA induced cells to enter mitosis and cells undergo apoptosis within 3 hours after entry into mitosis.

If the VDR is important for the DNA damage checkpoint delay, depletion of the VDR will reduce the length of the delay as determined by the time-lapse movies. It is possible that VDR does not act directly on the ATM-Chk1 pathway and its loss may not abrogate the delay with the same kinetics as seen with inhibitors of the checkpoint kinases. For example, if p21 is part of the delay mechanism, it may enhance the Chk1 mediated delay but loss of p21 would not inactivate Chk1 functions. These possibilities can be verified by probing lysates for levels of p21, phospho-ATM and -Chk1, as a function of time. The molecular information should provide a mechanistic explanation for the biological response.

The VDR may have nothing to do with the DNA damage checkpoint delay. The time lapse data will unambiguously show if cells die while arrested in S phase without ever entering mitosis. Alternatively, the VDR may promote the survival of cells that override the gemcitabine arrest. In the former case, the VDR is likely to suppress an apoptotic response during the checkpoint delay. This can be tested by probing lysates for levels of pro and anti-apoptotic proteins, some of which are reported to be regulated by the VDR. In the latter case, the VDR may promote survival of aneuploid cells through activation of the p38 stress pathway and the Akt pathway. This can be detected with phospho-p38 or -Akt antibodies. For either outcome, inhibitors of apoptosis and p38 and Akt will be added at appropriate times during the time lapse experiments to test if it alters cell response.

The time lapse approach will show how knockdown of the VDR affects the cellular response to gemcitabine. Movies will directly track the fates of individual cells, but the drawback is that a few hundred cells must be tracked to ensure statistically significant data, especially if a response is not highly uniform. However, despite improvements in high throughput imaging technology, clonogenic assays will still be conducted to obtain quantitative information about the response of a population of cells. Finally, as additional pancreatic cell lines are tested, the time lapse studies may reveal different responses that reflect different ways that VDR enhance survival after gemcitabine treatment. While the molecular differences that explain variability amongst cell lines may not be fully clarified, the different responses that are observed may reflect the spectrum of responses exhibited by a tumor.

Example 7

Determination of Whether Gemcitabine Sensitization by VDR is Dependent on p53

The experiments described in this Example will test if sensitization differs between p53-null cells versus cells that express DNA binding defective mutants of p53. The observation that depletion of VDR enhances cells to killing by gemcitabine is inconsistent with the anti-proliferative effects of vitamin D. This discrepancy may be reconciled if the transcription profile of VDR is altered in Panc1 and BXPC3 cells due to the expression of dominant gain of function mutations in p53. This possibility was demonstrated in a study that showed that DNA binding defective R175H p53 mutant disproportionately altered the transcriptional profile of VDR target genes.

This mutant along with a number of other similar p53 mutants interacted with the VDR and augmented the expression of some VDR target genes, but relieved the repression of some. Of significant interest, vitamin D3 reduced DNA damage (cisplatin and etoposide) induced apoptosis in cells expressing the mutant p53 alleles. As drug-induced apoptosis was restored upon knockdown of the mutant p53, the conclusion was that the mutant p53 converted the pro-apoptotic response of vitamin D into cytoprotective response. This was strengthened when expression microarray analysis showed that vitamin D3 in combination with mutant p53 upregulated survival genes and repressed pro-apoptotic genes that in combination may afford cytoprotective activity to the cells.

The Panc1 and BXPC3 cells used in the studies express the R273H and Y220C alleles of p53 that are defective for DNA binding. Significantly, the vitamin D3 response in multiple cancer cell lines that harbor the R273H mutation was shown to exhibit mutant p53-dependent anti-apoptotic activity. Addition of vitamin D3 to these cell lines reduced cisplatin and etoposide induced apoptosis because VDR was providing cytoprotective activity. Knockdown of mutant p53 reversed this activity and enhanced drug induced apoptosis by vitamin D. These observations may be of clinical importance as approximately 50% (12/27) of pancreatic tumors were reported to express p53 mutations within its DNA binding domain (Nigro J M et al. (1989) Nature 342:705-8).

Whether the knockdown of the mutant p53 alleles in the Panc1 and BXPC3 cells alters VDR-dependent sensitization to gemcitabine will be tested. siRNA transfections and shRNAs that deplete p53 will be used. Gemcitabine sensitization by VDR siRNA (or antagonists) will be compared between cells that express or are depleted of the mutant p53. If the ability of the pancreatic cancer cells to tolerate gemcitabine is due to an altered VDR transcriptional profile mediated by mutant p53, then depleting p53 may reduce gemcitabine sensitivity of cells to knockdown of the VDR. This outcome is predicated on the belief that the pro-apoptotic functions of the VDR are restored after depleting the mutant p53. This possibility can be confirmed by the expression of the pro and anti-apoptotic genes that were reported to be altered by the mutant p53. The caveat to this is that the gene patterns reported in breast and colon cancer cell lines will be relied upon, which patterns may differ from the patterns of pancreatic cancer cells. Thus, expression microarray experiments are proposed.

To complement the knockdown studies, restoring wild type p53 expression to the mutant knockdown cells will be employed to test whether and how it affects the VDR sensitization by gemcitabine. An RNAi resistant allele of wild type (WT) p53 will be introduced (adenovirus or retrovirus vectors) back to Panc 1 and BXPC3 cells stably expressing an shRNA that target the mutant p53. WT p53 is not thought to interact or alter the VDR transcriptional targets. Thus, the cells are expected to behave as with the mutant p53 knockdown cells.

VDR expression is induced by DNA damage through transcriptional activation by p73, a member of the p53 family. However, the dominant-negative p53 mutant can disrupt p73 functions and limit VDR upregulation by DNA damage. When mutant p53 expression is inhibited, p73 functions may be restored and VDR expression increased upon treatment with gemcitabine. VDR expression in Panc1 and BXPC3, and mutant p53 knockdowns, will be compared before and after gemcitabine treatment. As has been shown, the loss of mutant p53 can convert the transcriptional profile of the VDR from a cytoprotective signature to an apoptotic signature. In fact, depletion of mutant p53 from breast and colon cancer cells restored vitamin D3 dependent sensitivity to cisplatin and etoposide. Collectively, these data suggest that when mutant p53 is eliminated, the anti-proliferative functions of the VDR are restored. It will be tested whether depletion of mutant p53 from Panc1 and BXPC3 cells can convert their sensitivity to gemcitabine (or the DNA damaging agents) to be enhanced by vitamin D.

If the results support the idea that VDR functions in drug response depend on the context of p53 mutation, the analysis will be expanded to include additional pancreatic cancer cell lines with different p53 status (http://p53.free.fr/Database/Cancer_cell_lines/Pancreatic_cancer.html). These studies will provide a mechanistic understanding that will lead to future xenograft studies. The studies may provide a rationale for choosing between VDR agonists or antagonists to enhance the efficacy of gemcitabine or other cytotoxic drugs in pancreatic cancer patients.

Example 8

Examination of how p53 Status Alters the Expression of VDR Target Genes

Mutant p53 was shown to alter the transcriptional profile of VDR target genes in the SKBR3 breast cancer cells. Expression microarray analysis of four different states (+/−mutant p53; +/− vitamin D treatment) led to the realization that mutant p53 altered the transcription program of vitamin D. To understand how mutant p53 alters response of pancreatic cancer cells to gemcitabine, a similar series of microarray experiments are proposed.

The study will be conducted with BXPC3 adenocarcinomas and subclones that are depleted of mutant p53 by stable integration of an shRNA construct. Cells are exposed to vitamin D for various times to optimize peak expression of target genes (CYP24A, IGFB3) by RT-per. RNA extracted from cells treated and untreated with vitamin D are analyzed by microarray. The experiments will be outsourced to a vendor with expertise in microarray analysis.

The expression in the absence of p53 and no vitamin D for each gene in the genome will be determined from the average of two experiments and used as the baseline. The effects of mutant p53 and vitamin D on gene expression are next determined and expressed as the fold change over baseline. Ratios of +/−vitamin D in cells depleted of mutant p53 are plotted on one axis. The other axis is the ratios of +/−vitamin D on mutant p53 expressing cells. Data are plotted on a log 2 scale. Genes unaffected by p53 and vitamin D should fall along in the center (no difference between different treatments).

In the SKBR3 study, genes that showed >4-fold difference was grouped into three clusters. These clusters include genes highly expressed in the presence of mutant p53 and vitamin D, genes repressed in the absence of mutant p53, and genes repressed by both mutant p53 and vitamin D. Comparison of the clusters would identify VDR regulated genes whose expression are altered by mutant p53.

Expression patterns will be compared with the SKBR3 cells to identify genes in common and those that may be unique to pancreatic cancer. The unique genes may provide further molecular information about how mutant p53 alters the response of pancreatic cancer cells to drugs. Future efforts will be to use the genes from the different clusters to probe expression patterns in other pancreatic cancer cell lines to assess the universality of the response. Given that vitamin D is being tested as an anti-cancer drug, it is important to recognize that mutant p53 status may be a strong predictor of treatment outcomes.

The invention is not limited to the embodiments described and exemplified above, but is capable of variation and modification within the scope of the appended claims.

We claim:

1. A method for killing tumor cells expressing the vitamin D receptor, comprising antagonizing the vitamin D receptor in the tumor cells, and contacting the tumor cells with an amount of gemcitabine effective to damage DNA in the tumor cells, wherein the combination of antagonizing the vitamin D receptor and gemcitabine exhibits therapeutic synergy in killing the tumor cells.

2. The method of claim 1, wherein the tumor cells are pancreatic tumor cells, lung tumor cells, breast tumor cells, ovarian tumor cells, lymph node tumor cells, bladder tumor cells, prostate tumor cells, or esophageal tumor cells.

3. The method of claim 1, wherein the tumor cells are pancreatic tumor cells.

4. The method of claim 1, wherein antagonizing the vitamin D receptor comprises contacting the tumor cells with an effective amount of a compound that inhibits the biologic activity of the vitamin D receptor.

5. The method of claim 4, wherein the compound is a vitamin D analog.

6. The method of claim 1, wherein the tumor cells expressing the vitamin D receptor are resistant to gemcitabine.

7. The method of claim 1, further comprising inhibiting the expression or the biologic activity of p53-binding protein 1 (53BP1) in the cells.

8. A method for killing tumor cells expressing the vitamin D receptor, comprising transforming the tumor cells with a nucleic acid molecule that inhibits the expression of the vitamin D receptor in the tumor cells, and then contacting the tumor cells with an amount of gemcitabine effective to damage DNA in the cells, wherein the combination of inhibiting the expression of the vitamin D receptor and gemcitabine exhibits therapeutic synergy in killing the tumor cells.

9. The method of claim 8, wherein the tumor cells are pancreatic tumor cells, lung tumor cells, breast tumor cells, ovarian tumor cells, lymph node tumor cells, bladder tumor cells, prostate tumor cells, or esophageal tumor cells.

10. The method of claim 8, wherein the tumor cells are pancreatic tumor cells.

11. The method of claim 8, wherein the tumor cells are resistant to gemcitabine.

12. The method of claim 10, wherein the pancreatic tumor cells are resistant to gemcitabine.

13. The method of claim 8, wherein the nucleic acid molecule is a siRNA that specifically hybridizes under stringent conditions to the mRNA encoding the vitamin D receptor.

14. The method of claim 3, wherein the pancreatic tumor cells are resistant to gemcitabine.

15. The method of claim 3, wherein the method comprises antagonizing the vitamin D receptor in the pancreatic tumor cells by contacting the cells with a vitamin D analog in an amount effective to antagonize the vitamin D receptor, and then contacting the cells with an amount of gemcitabine effective to damage DNA in the cells, wherein the combination of the vitamin D analog and gemcitabine exhibits therapeutic synergy in killing the tumor cells.

16. The method of claim 15, wherein the pancreatic tumor cells are resistant to gemcitabine.

17. A method for treating a pancreatic tumor comprising cells expressing the vitamin D receptor in a human patient in need thereof, comprising administering to the patient a vitamin D receptor antagonist in an amount effective to antagonize the vitamin D receptor in the cells, and administering to the patient gemcitabine in an amount effective to damage DNA in the cells, wherein the combination of the vitamin D receptor antagonist and gemcitabine exhibits therapeutic synergy in treating the pancreatic tumor in the patient.

18. The method of claim 17, wherein the vitamin D receptor antagonist is a vitamin D analog.

19. The method of claim 17, wherein the cells are resistant to gemcitabine.

20. The method of claim 18, wherein the cells are resistant to gemcitabine.

* * * * *